(12) United States Patent
Cragg

(10) Patent No.: US 6,315,789 B1
(45) Date of Patent: Nov. 13, 2001

(54) MEDICAL DEVICE ANCHORING SYSTEM AND METHOD

(76) Inventor: Andrew H. Cragg, 4502 Edina Blvd., Edina, MN (US) 55424

(*) Notice: Subject to any disclaimer, the term of this patent is extended or adjusted under 35 U.S.C. 154(b) by 0 days.

(21) Appl. No.: 09/246,628

(22) Filed: Feb. 8, 1999

(51) Int. Cl.⁷ .................................................. A61B 17/04
(52) U.S. Cl. ........................... 606/232; 606/213; 604/175
(58) Field of Search ................................ 606/190, 232, 606/233, 231, 224, 225, 227, 213; 604/51–53, 174, 175, 106, 176, 177

(56) References Cited

U.S. PATENT DOCUMENTS

| | | | |
|---|---|---|---|
| 4,196,883 | 4/1980 | Einhorn et al. | 248/546 |
| 4,488,877 | 12/1984 | Klein et al. | 604/175 |
| 4,516,968 | 5/1985 | Marshall et al. | 604/174 |
| 4,669,473 | 6/1987 | Richards et al. | 128/334 |
| 4,685,901 | 8/1987 | Parks | 604/96 |
| 4,705,040 | 11/1987 | Mueller et al. | 128/334 |
| 4,781,693 | 11/1988 | Martinez et al. | 604/175 |
| 5,007,900 | 4/1991 | Picha et al. | 604/106 |
| 5,041,085 | 8/1991 | Osborne et al. | 604/51 |
| 5,041,129 | 8/1991 | Hayhurst et al. | 606/232 |
| 5,123,914 | 6/1992 | Cope | 606/232 |
| 5,151,086 | 9/1992 | Dub et al. | 604/51 |
| 5,259,367 | 11/1993 | Kirby et al. | 128/8 |
| 5,267,968 | 12/1993 | Russo | 604/174 |
| 5,267,970 | 12/1993 | Chin et al. | 604/175 |
| 5,273,529 | 12/1993 | Idown | 604/49 |
| 5,279,575 | 1/1994 | Sugarbaker | 604/174 |
| 5,307,924 | 5/1994 | Manosalva et al. | 206/63.3 |
| 5,318,543 | 6/1994 | Ross et al. | 604/164 |
| 5,341,823 | 8/1994 | Manosalva et al. | 128/898 |
| 5,352,198 | 10/1994 | Goldenberg et al. | 604/95 |
| 5,419,764 | 5/1995 | Roll | 604/95 |
| 5,458,583 | 10/1995 | McNeely et al. | 604/96 |
| 5,531,678 | 7/1996 | Tomba et al. | 604/51 |
| 5,531,699 | 7/1996 | Tomba et al. | 604/164 |
| 5,626,614 | 5/1997 | Hart | 606/232 |

Primary Examiner—Michael Buiz
Assistant Examiner—Lien Ngo
(74) Attorney, Agent, or Firm—Joseph F. Breimayer

(57) ABSTRACT

Methods and apparatus for anchoring percutaneous devices, e.g., tubes or catheters or leads, extending percutaneously through a percutaneous passageway from the skin of a patient to a subcutaneous location or body cavity or tract or lumen from movement further into the body or retraction out of the body. An implantable anchor comprising an anchor body and a tensioning filament is inserted through the percutaneous passageway and deployed subcutaneously with the anchor body in engagement with body tissue in a manner that inhibits it from being retracted through the passageway. The tensioning filament extends from the anchor body and alongside the percutaneous device body through the percutaneous passageway and tension is applied to it to draw the deployed anchor against subcutaneous body tissue and toward the patients skin. The tensioning filament is coupled with an attachment mechanism secured against the percutaneous device body outside the patient's skin at a location adjacent to the patient's skin. The assembly of the deployed anchor within the patient's body with the external attachment mechanism inhibits advancement or retraction of the percutaneous device body through the percutaneous passageway. When use of the percutaneous device is to be discontinued, the tensioning filament can be severed outside the skin, to release and retract the percutaneous device and attachment mechanism as a unit from the percutaneous passageway, releasing tension on the anchor body. The retraction filament is then retracted, causing the anchor body of the anchor to pivot into axial alignment with the percutaneous passageway, and the anchor body can then simply be pulled out through the percutaneous passageway. The percutaneous device is preferably a gastrostomy or jejunostomy or gastro-jejunal catheter having a catheter body lumen and a disposable inner liner fitted therein and engaging the anchor body during insertion through the percutaneous passageway and retractable to release the anchor within the patient's stomach or small intestine.

37 Claims, 11 Drawing Sheets

MEDICAL DEVICE ANCHORING SYSTEM AND METHOD

FIELD OF THE INVENTION

The present invention relates generally to methods and apparatus for anchoring medical devices extending through a natural body tract or lumen or a surgically created percutaneous passageway through a patient's skin, including tubes, catheters, or electrical leads, to a subcutaneous location or to a body cavity or tract or lumen from movement further into the body or retraction out of the body, and particularly to such a method and apparatus for anchoring such a device extending into a patient's stomach and/or into a patient's small intestine.

BACKGROUND OF THE INVENTION

In a number of surgical or medical procedures, medical devices, e.g., tubes or catheters or electrical signal conducting leads, are introduced into the body of a patient, typically on a temporary basis to access a body cavity, vessel, duct or lumen or a body organ or muscle for diagnostic or therapeutic purposes or to provide drainage of a body organ or cavity. A variety of fixation mechanisms and systems are provided to maintain the distal end of the introduced catheter, tube or lead at the desired site that is initially accessed while allowing the patient to be ambulatory or to have some freedom of movement. If a fixation method or system is not provided, patient movement or interference with clothing or the bed, etc., can apply retraction or advancement forces to the implanted or inserted catheter, tube or lead causing it to be either further advanced or retracted possibly endangering the patient or causing patient discomfort and failure to perform its intended function. The fixation mechanisms operate either passively or require activation during the implantation or insertion procedure. The fixation mechanism must be disabled or otherwise released to allow retraction of the catheter, tube or lead from the body when its purpose is served.

In the field of temporary cardiac pacing or monitoring, electrical leads are introduced percutaneously through the vascular system to locate distal pace/sense electrode(s) within a heart chamber or cardiac vessel or are extended from the exterior of the heart through the skin incision following cardiac surgery to conduct pacing pulses and the sensed electrogram between the heart and an external pacemaker pulse generator. Similarly, electrical leads are introduced percutaneously into selected muscle groups or into the spinal column to provide muscle and nerve stimulation and other sensor bearing leads can be inserted into the body to sense other physiologic conditions, e.g., temperature, blood gases, blood pressure or the like. The externally extending proximal portions of such leads are typically held in place by adhesive bandages or the like applied over the lead body or winged flaps of the lead body and against the patient's skin. In some instances, the lead distal tips are configured to provide some resistance to accidental withdrawal. Withdrawal is effected by traction applied to the lead body outside the skin. Similar methods and approaches have also been employed to secure drainage tubes or catheters extending subcutaneously into a body cavity, lumen, vessel or duct, etc.

Gastrostomy tubes or catheters are placed percutaneously through the patient's skin, the underlying abdominal wall and the gastric or stomach wall and into the stomach cavity in order to provide nutrients to a patient who is unable to chew or swallow food as described, for example, in U.S. Pat. Nos. 4,705,040, 5,007,900, 5,151,086, 5,273,529 and 5,458,583, all incorporated herein by reference. In this procedure, it is necessary to ensure that the distal end of the gastrostomy catheter remains within the stomach, and that the stomach wall is sealed against the catheter to inhibit leakage of stomach fluids into the peritoneal cavity or all the way through the puncture. The stomach wall and the abdominal wall are pulled together and then held in contact by insertion of a plurality of T-fasteners at spaced apart locations to form a contact area or field through which the gastrostomy catheter can be introduced via a stoma tract as disclosed in the above-incorporated '040, '086 and '583 patents. It may be necessary to leave the gastrostomy catheter in place for weeks or months, and the stomach wall and abdominal wall adhere together and a tissue layer forms around the stoma tract.

The gastrostomy catheter itself is held in place extending through the stoma tract typically by adhesion to the patient's skin and/or by use of various forms of stabilization and sealing mechanism. For example, in the above-incorporated '529 or '583 patents, the gastrostomy catheter includes an expandable Mallecot tip or an inflatable balloon, respectively, adapted to be received in the stomach cavity and expanded therein to bear against the stomach wall. External retention rings surrounding the catheter body proximal to the balloon bear against the patient's skin around the stoma tract. In the '583 patent, the balloon can be inflated within the stomach cavity, and the retention ring that can be pushed against the skin to draw and compress the annular balloon against the stomach wall surrounding the stoma tract and to seal it from leakage. In the '900 patent, the gastrostomy catheter distal end is formed with a resilient T-bar that normally extends transverse to the catheter axis but can be straightened out during insertion through the stoma tract and can then be released within the stomach to inhibit retraction. An external ring is also provided that can be applied against the skin to compress the stomach wall and abdominal wall together in the area surrounding the stoma tract and catheter body extending therethrough. In these approaches, the location of distal tip of the gastrostomy or jejunostomy catheter in the stomach or small intestine is fixed adjacent to the stoma tract by operation of the fixation mechanism and cannot be inserted to a desired site.

Similar procedures can be followed in performing a jejunostomy to access the small intestine using a jejunostomy tube or catheter that has a longer catheter body than a gastrostomy catheter as described in the above-incorporated '086 patent. A combined gastrostomy and jejunostomy or gastro-jejunal catheter is also known for accessing both the stomach cavity and the small intestine. Generally, short and long catheter lumens are incorporated into the catheter body, in either a side-by-side or co-axial arrangement of an inner and outer catheter body. The shorter catheter lumen terminates in end and/or side holes located in the stomach cavity, and the longer catheter lumen terminates in end and/or side holes located in the small intestine. Such a co-axial gastro-jejunal tube or catheter is disclosed in U.S. Pat. No. 4,685,901, incorporated herein by reference. In the '901 patent, a balloon on the outer catheter is inflated in the stomach and an exterior plate is brought to bear against the skin to draw the balloon against the stoma opening to close it and to hold the gastro-jejunal tube in place.

Drainage tubes or catheters are frequently introduced percutaneously through a surgically created tract into a body cavity or organ to simply provide drainage of fluids that accumulate therein following surgery, for example. Drainage catheters are usually simply taped to the skin at the incision without any stabilization provision or system. However, in some cases stabilization is provided using an inflatable balloon and external ring system as described above or an expandable Mallecot tip of the type described in the above-incorporated '529 patent or a Cope loop that is formed by a retraction of a distal section of the catheter within the cavity into a curve by retracting a filament extending outside the skin.

Other tubes or catheters are inserted into existing body tracts, vessels or lumens, etc. In urinary catheterization procedures, catheters are introduced through the uretha into the bladder to facilitate drainage after an injury or surgical procedure. Typically, the distal portion of the catheter has an inflatable balloon attached to it that is inflated in the bladder after the urinary catheter is inserted therein to resist unintentional retraction. Naso-gastric catheters are extended to the stomach cavity through a patient's nasal cavity and esophagus, and are often held in place by taping an exposed section about the patient's nose.

Some of these attachment mechanisms are bulky and difficult to use in a body vessel, duct or tract or surgically created incision or stoma tract or the like and frequently require them to be dilated to pass the catheter or tube and its internal retention mechanism through them. For example, inflatable balloon retention mechanisms can increase the diameter of a catheter by 2–4 French when the balloon is deflated.

In addition, these internal retention mechanisms (other than simply employing adhesive tape or the like around the body of the catheter, tube or lead and against the patient's skin) are formed as part of the catheter, tube or lead body. Their retention strength and capability to be employed in a given application are limited by the size and strength of the catheter body. If the catheter body is necessarily soft and pliant, it may provide a weak support for the internal attachment mechanism.

A number of such problems exist with current retention mechanisms used within the stomach cavity to retain the gastrostomy or jejunostomy or combined gastro-jejunal tubes or catheters in place. The inflatable balloons add to the size of the catheter body when deflated and cause the stoma cavity to be dilated as the deflated balloon is inserted through it. Then, leakage of stomach acid into the peritoneal cavity or onto the skin can occur through the dilated stoma around the catheter body. To avoid this problem, the balloon wall is made of thin, stretchable material. Such balloon walls are fragile and can break during installation and are degraded over time by stomach acids to the point where they break. The expandable Mallecot tip is bulky and can be difficult to retract through the stoma tract when it is desired to do so, but paradoxically can sometimes fail to retain the catheter in the stoma tract. The filament employed to bend the catheter distal end into the Cope loop often breaks where it is attached to the catheter tip because the catheter body has to be soft and pliable. Tension applied to the filament to maintain the Cope loop can sometimes quickly cause it to separate from the catheter tip, causing the tip to straighten and the catheter to fall out or be drawn out of the stoma tract. All of these retention mechanisms also suffer from low "pull strength", that is the force required to overcome the retention mechanism and to pull the catheter out of the stoma tract is relatively low. Often, these catheters are inadvertently pulled out of the stoma tract, causing stomach acids to escape and causing discomfort to the patient.

The gastrostomy or jejunostomy or combined gastro-jejunal tube or catheter is intended to be coupled at its proximal end to a nutrient container and periodically used to infuse liquid nutrients through its lumen and into the stomach or small intestine cavity. The catheter lumen can become clogged over weeks or months of usage, and it is inconvenient or not possible to clean it. Consequently, it may be necessary to replace the gastrostomy or jejunostomy catheter simply to provide a usable catheter lumen.

SUMMARY OF THE INVENTION

Accordingly, it is an object of the present invention to provide an improved retention mechanism for a catheter, tube or lead extending from exterior to a patient's skin through a natural or surgically created percutaneous passageway and into a subcutaneous location (hereinafter referred to as a "percutaneous device" regardless of the passageway).

It is a particular object of the present invention to provide a system separate from the percutaneous device body for providing its secure retention with body tissue at the subcutaneous location and against the patient's skin that can be easily deployed and fixed to the percutaneous device body.

Similarly, it is a further object of the present invention to provide such a system separate from the percutaneous device body for providing its secure retention within the body cavity and against the patient's skin that can be easily released from the percutaneous device body and retracted from the patient's body.

These and other objects of the invention are realized in a percutaneous assembly and method of use of the assembly for fixing a percutaneous device at its point of percutaneous insertion into a patient's body. The assembly comprises a percutaneous device body and an implantable anchor comprising an anchor body and a tensioning filament attached to the elongated anchor body adapted to be inserted through the percutaneous passageway and deployed subcutaneously in engagement with body tissue independently of and extending transversely to the percutaneous device body and the percutaneous passageway. When so positioned, the tensioning filament extends through the percutaneous passageway to the exterior of the skin. An attachment mechanism of the percutaneous device body is adapted to be located adjacent to the patient's skin to receive and secure the tensioning filament to the percutaneous device body. This assembly of the deployed anchor body extending transverse to the percutaneous device body and the tensioning filament attached to the percutaneous device body inhibits advancement or retraction of the percutaneous device body through the percutaneous passageway.

The distal end of the flexible tensioning filament is coupled to the elongated, relatively rigid, tubular anchor body intermediate its opposite ends, so that that tension applied to the tensioning filament causes the anchor body, that is inserted axially through the percutaneous passageway, to pivot and extend transversely to the percutaneous passageway and percutaneous device body extending therethrough. The anchor body length exceeds the width of the percutaneous passageway, and the tensioning filament maintains it extending across and bridging the percutaneous passageway.

In certain instances, the anchor body cannot be left in place after withdrawal of the percutaneous device or will not pass through the intestinal tract, a withdrawal filament is optionally coupled to one end of the tubular anchor body and extended through the percutaneous passageway alongside the percutaneous device body for enabling axial alignment of the anchor body to and withdrawal of the anchor body through the percutaneous passageway after use of the percutaneous device is finished.

In use, the percutaneous passageway is either surgically created or located, and the anchor is introduced through it and into a body cavity or subcutaneous space while its anchor body is maintained axially in alignment with the percutaneous passageway such that a distal end of the anchor body extends distally and the tensioning filament and withdrawal filament (if present) trail proximally through the percutaneous passageway. The percutaneous device and anchor body are advanced through the percutaneous passageway, and the anchor body is released and pivoted to extend across and bridge the percutaneous passageway. The proximal end of the tensioning filament is retracted and attached to the percutaneous device.

The axial alignment and introduction of the anchor is preferably effected by a coupling means supporting the anchor body at the distal end of the percutaneous device body and in axial alignment with the axis of the percutaneous device body so that the tensioning filament and the withdrawal filament (if present) extend proximally alongside the percutaneous device body. The free ends of the tensioning filament and the withdrawal filament trail behind the advanced anchor body and extend through the percutaneous passageway outside the patient's body. When the anchor body is located distal to the subcutaneous body tissue it is to be anchored against, it is released from the distal end of the percutaneous device body. The released anchor body orientation is changed to be transverse to and extend laterally across the percutaneous device body and bridging the percutaneous passageway.

The percutaneous device body preferably is formed with a percutaneous device lumen extending between proximal and distal lumen end openings at the percutaneous device proximal and distal ends, respectively, that can be employed to infuse or withdraw fluids into or from a body site and/or receive a stylet or guidewire to facilitate advancement of the percutaneous device through the percutaneous passageway and to the desired body site. To facilitate implantation of the anchor, the anchor body is preferably formed with an elongated anchor body channel extending between the anchor body proximal end and the anchor body distal end. The stylet or guidewire can be inserted through the percutaneous device lumen and extended through the anchor body channel to facilitate advancement of the anchor axially through the percutaneous passageway and lateral release of the anchor body from the guidewire while leaving the guidewire in place.

A number of mechanisms can be employed to retain and release the anchor body from the percutaneous device body. In one embodiment, a disposable, tubular, inner sleeve or liner having a liner lumen and a liner outer diameter sized to fit within the percutaneous device lumen is fitted within the percutaneous device lumen. The inner liner can be removed and replaced if the liner lumen becomes obstructed in chronic use. The inner liner has a length that allows the liner distal end to extend to the percutaneous device distal end when it is placed into the percutaneous device lumen. The tubular anchor body is sized to abut against the percutaneous device distal end, and a short, reduced diameter, proximal section of the anchor body is sized to fit snugly within the liner lumen. The anchor body is supported to extend axially and distally from the distal end of the assembled percutaneous device body and the inner liner upon insertion of the short proximal section of the anchor body through the liner lumen distal end opening and into the liner lumen. The percutaneous assembly can be advanced distally through the percutaneous passageway over a guidewire in the manner described above. The inner liner is retracted, releasing the short proximal end of the anchor body and allowing it to fall free into the body cavity after the anchor body and a distal portion of the percutaneous device body are inserted through the percutaneous passageway into the body cavity. In this manner, the disposable inner liner can be manipulated to also function as a support and release mechanism for supporting the anchor body during its advancement through the percutaneous passageway and to release it at the desired body site.

In other applications not employing the disposable inner liner, the short proximal anchor body section is sized to fit snugly within the distal end opening of the percutaneous device lumen. The percutaneous assembly can be advanced distally through the percutaneous passageway over a guidewire in the manner described above. In one form of coupling and release element, a pusher rod or catheter is advanced through the percutaneous device lumen proximal end opening and distally within the percutaneous device lumen (optionally over the guidewire) to push the short proximal anchor body section out of the distal end opening of the percutaneous device lumen. In another form, a retractable rod or filament or the like can be retracted from coupling engagement with the anchor body to release it from alignment with the percutaneous device body.

The attachment mechanism for attaching the tensioning filament to the percutaneous device body can take a variety of forms. In an illustrated preferred embodiment, a side arm is fixed to the percutaneous device body through which a proximal section of the tensioning filament extends. The percutaneous device body and the anchor are inserted through the percutaneous passageway with the tensioning filament and withdrawal filament (if present) trailing alongside and extending outside the body. The anchor body is released as described above. All of the percutaneous device body distal to the side arm is inserted through the percutaneous passageway and the percutaneous device distal end is positioned at the desired body site. A skin abutting stop may be provided adjacent to the side arm to inhibit movement of the side arm into the percutaneous passageway. The proximal portion of the tensioning filament extending outside the percutaneous passageway is threaded through a crimp sleeve of the side arm. The proximal end of the tensioning filament is manually drawn through the crimp sleeve to take up slack and snug the elongated tubular anchor body against the subcutaneous body tissue extending laterally to the percutaneous device body and bridging the percutaneous passageway. Then, the physician employs a tool, e.g., a forceps, to crimp the crimp sleeve against the tensioning filament to maintain the applied tension and relationship of the anchor body to the attachment mechanism.

In other embodiments, the attachment mechanism can be in the form of a collar that is movable along the percutaneous body and fixed against a proximal stop when the slack is taken out of the tensioning filament. The crimp sleeve can be formed as part of the collar.

The tensioning filament can be severed outside the skin to release tension on the anchor body and allow the percutaneous device body to be retracted through the percutaneous passageway when use of the percutaneous device is to be discontinued. The withdrawal filament, if present is then retracted, causing the anchor body to pivot into axial alignment with the percutaneous passageway. The anchor body is then simply be pulled out through the percutaneous passageway. In a gastrostomy or jejunostomy catheter application, the anchor body can simply be left in the stomach or small intestine and passed through the intestinal tract of the patent.

In the gastrostomy or jejunostomy or gastro-jejunal catheter anchoring application, the percutaneous passageway or stoma tract can be effected in a field previously prepared using a plurality of T-fasteners to draw the stomach wall skin and abdominal wall together in the manner described in the above-incorporated '040, '086, and '583 patents. Then, the above-described procedure and system can be used to locate the percutaneous device distal end and the anchor body in the stomach cavity. In this case, the anchor body is drawn against the stomach wall, and the tensioning filament is coupled with the attachment mechanism located outside the stoma tract and adjacent to or bearing against the patient's skin.

Alternatively, the deployment of the anchor body across the stoma tract opening within the stomach in accordance with the present invention may itself prove sufficient to seal the stoma tract from leakage of stomach fluids into the peritoneal cavity, thereby eliminating the need for preparation of the field using the plurality of T-fasteners.

The same method and system can be employed to anchor drainage tubes, electrical leads and any catheters inserted into other body lumens or cavities through a variety of body passageways, including natural ducts, vessels or tracts or surgically created passageways wherever it is possible to locate the anchor body into a desired body site to bear against body tissue. In some instances, e.g., during the stabilization of an electrical lead or catheter that extends a distance to the desired site in the body, it may be necessary to form a subcutaneous cavity adjacent the skin incision to receive the anchor body.

The method and system of the present invention can be employed in a wide variety of situations to stabilize such percutaneous device bodies that have a wide range of body lengths and diameters. The size and weight of the anchor body can be made proportional to the force or strength required to stabilize a particular percutaneous device body. The percutaneous device body can be formed of materials allowing it to be flexible and capable of being advanced through tortuous routes in the body since it is not carrying or attached to the internally disposed anchor. The anchor body can be formed of higher durometer material so that it is relatively stiff and resistant to being flexed when deployed across the percutaneous passageway.

At the same time, since the anchor is independent of the particular percutaneous lead body, it does not add to the size or is not unnecessarily restricted by the size of the percutaneous device body. The axial alignment and support of the anchor body extending distally from the percutaneous device body does not increase the overall diameter of the tubular assembly, thereby maintaining a low profile. The low profile allows the insertion through the percutaneous passageway to be accomplished without use of a larger diameter, peel-away sheath, introducer as is necessary when employing the Mallecot tip or an inflatable balloon retention mechanism in certain cases. Therefore, dilation of the percutaneous passageway to accommodate such an introducer, and the additional cost of the introducer, is avoided.

A great improvement in retention force or pull strength resisting retraction can therefore be provided while not complicating the implantation of the percutaneous device body. When use is to be terminated, the percutaneous device body and its anchoring system are easily withdrawn from the percutaneous passageway.

This summary of the invention and the objects, advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

Other objects, advantages and features of the present invention will be readily appreciated as the same becomes better understood by reference to the following detailed description when considered in connection with the accompanying drawings (which are not necessarily to scale), in which like reference numerals designate like parts throughout the figures thereof and wherein.

DETAILED DESCRIPTION OF THE PREFERRED EMBODIMENTS

Figure 8:
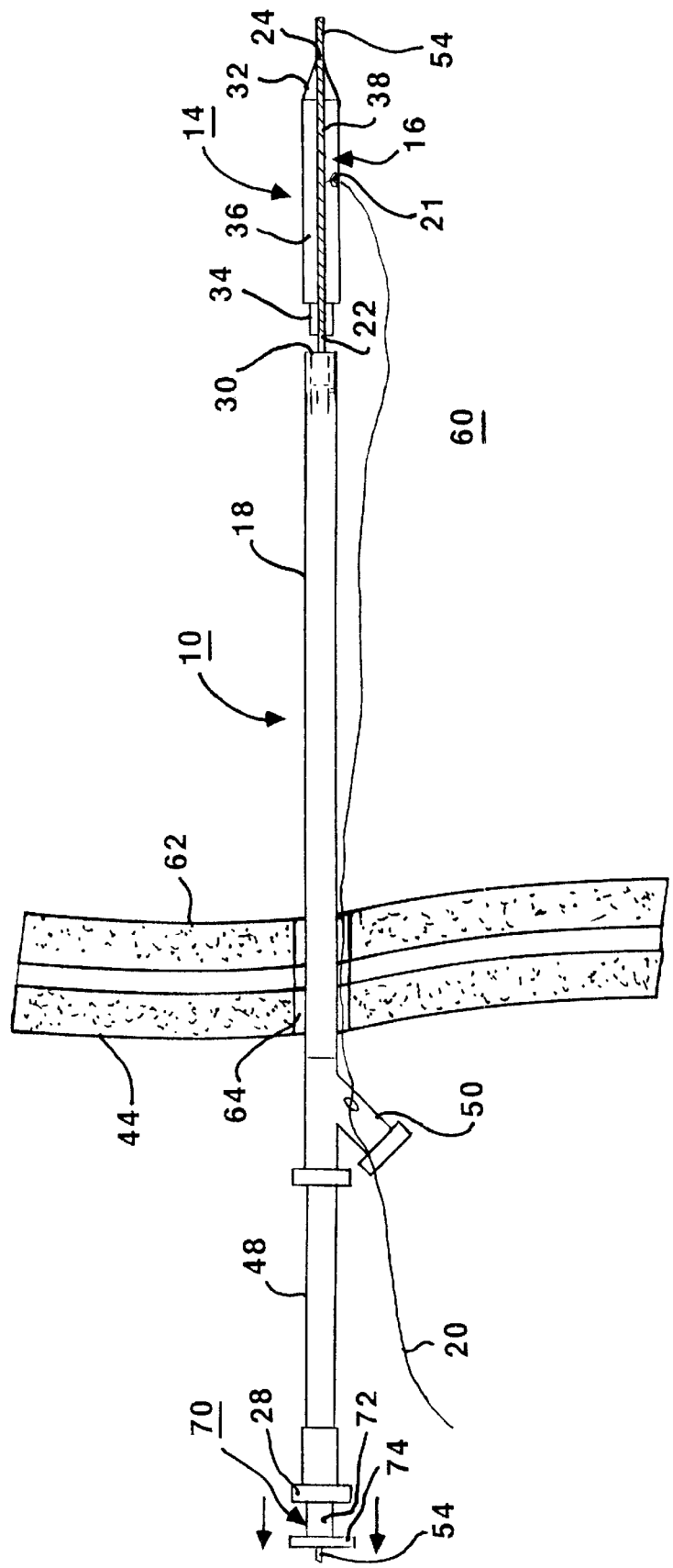
FIG. 8 is a side plan view of the assembly of FIG. 6 (with the guidewire not shown for clarity of illustration) showing the inner liner retracted proximally to release the anchor body.
Figure 9:
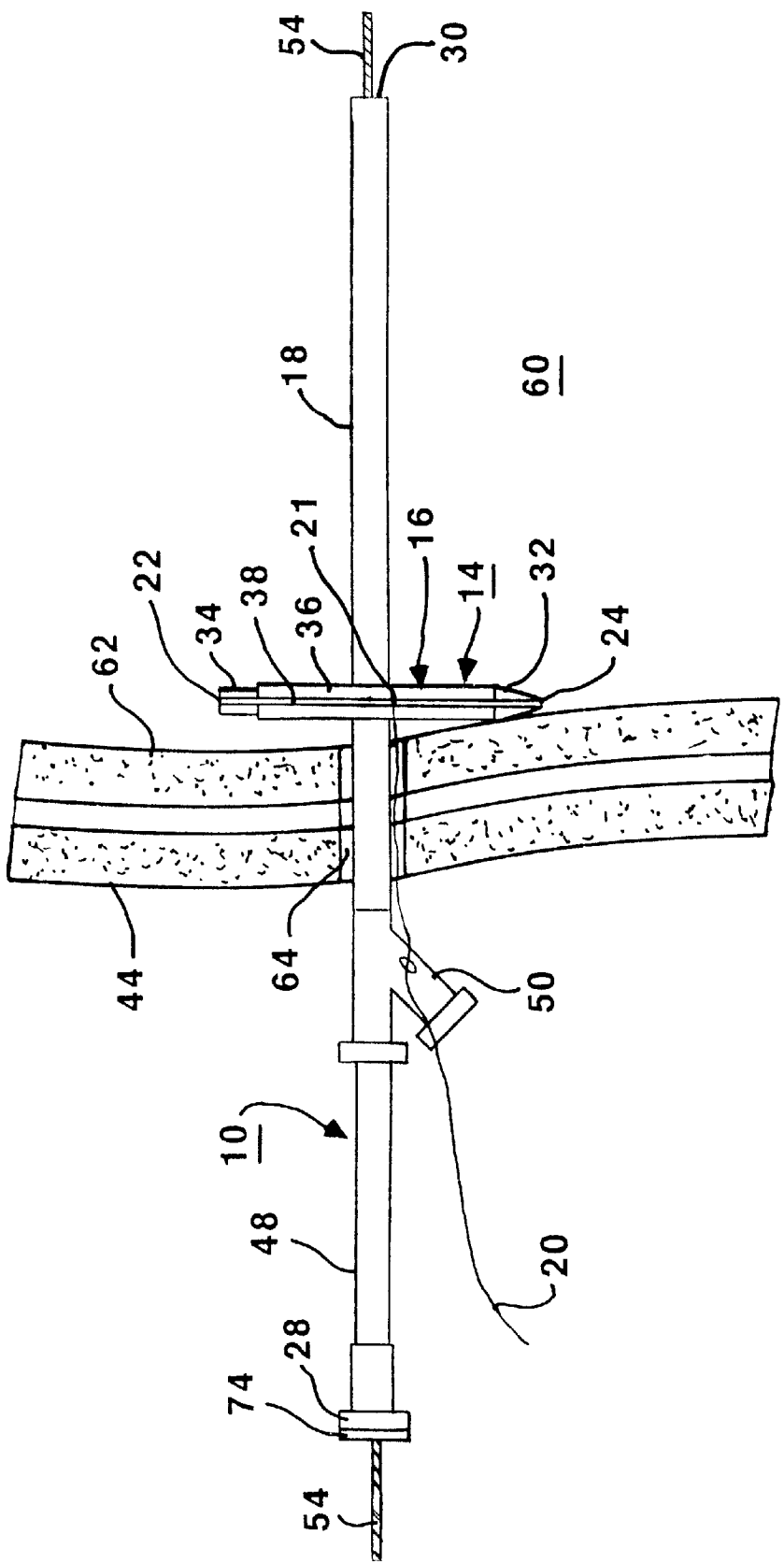
FIG. 9 is a side plan view of the assembly of FIG. 6 showing the anchor body drawn back against the stomach wall and across the stoma tract opening and the tensioning filament attached to the attachment mechanism coupled with the gastrostomy catheter body adjacent the patient's skin.
Figure 10:
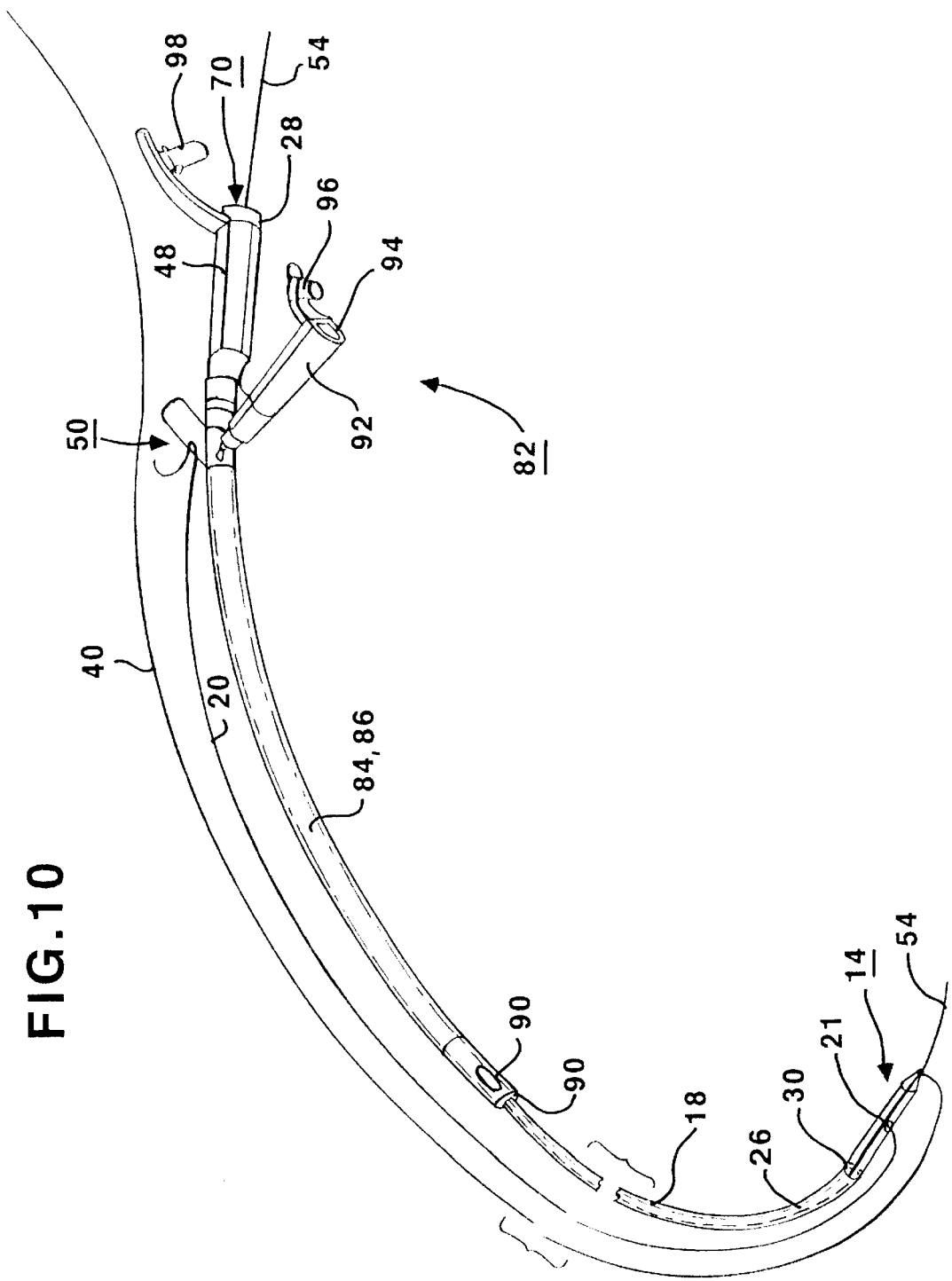
FIG. 10 is a perspective view of the assembly of a two lumen, co-axial, gastro-jejunal tube or catheter having a disposable inner liner and anchor of a further preferred embodiment of the present invention with the elongated anchor body supported at the distal end and axially aligned with the jejunostomy catheter in the manner depicted in FIGS. 6 and 7.
Figure 11:
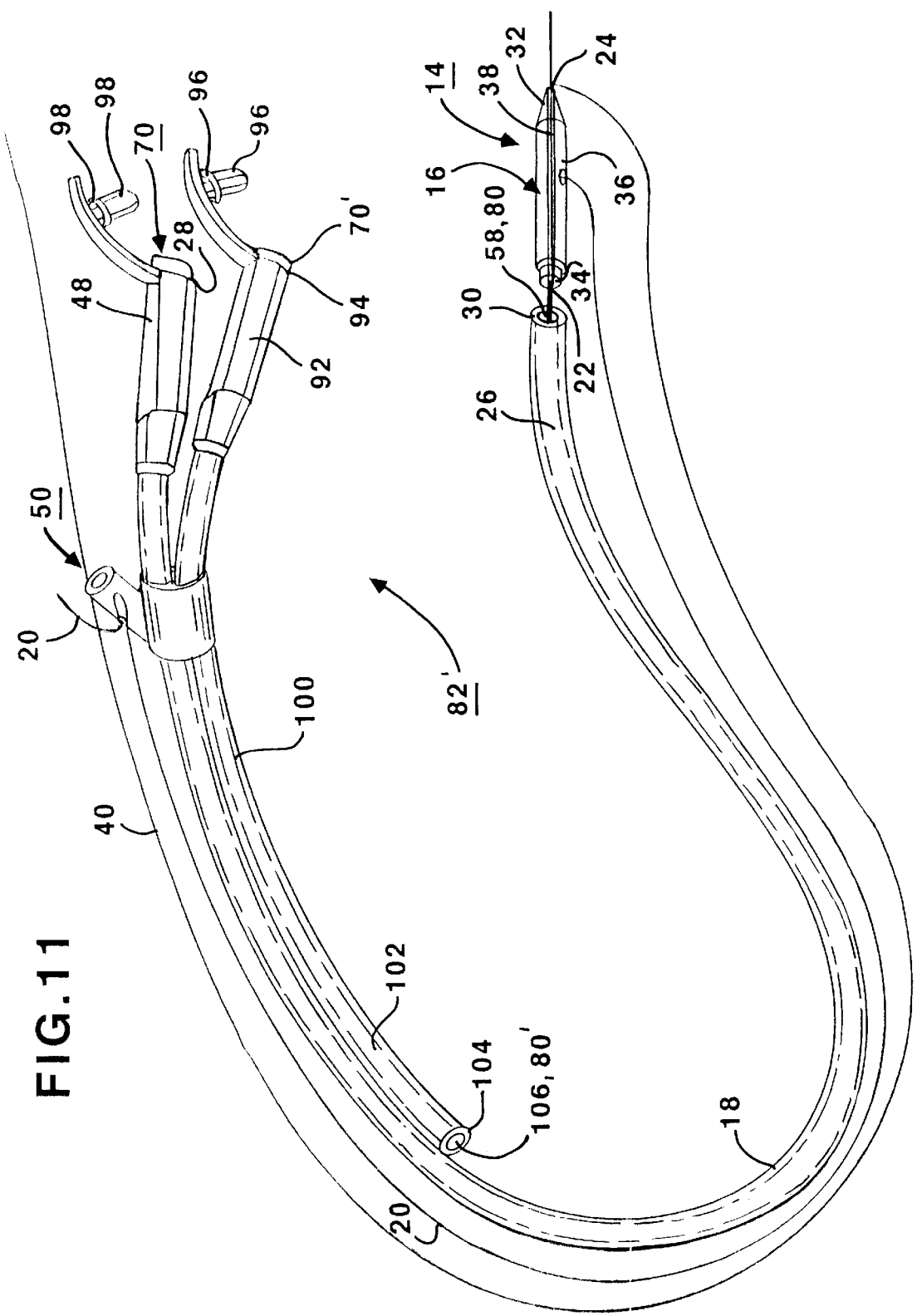
FIG. 11 is a perspective view of the assembly of a two lumen, side-by-side, gastro-jejunal tube or catheter having disposable inner liners in each lumen and an anchor of a further preferred embodiment of the present invention with the elongated anchor body adapted to be supported at the distal end and axially aligned with either the gastrostomy catheter or the jejunostomy catheter in the manner depicted in FIGS. 6 and 7.

The preferred embodiment of the present invention is realized in a method and system for fixing a percutaneous device at its point of percutaneous insertion through a percutaneous passageway into subcutaneous site of a patient's body illustrated in a general embodiment of FIGS. 1–5, in a gastrostomy/jejunostomy catheter embodiment of FIGS. 6–9, and in a gastro-jejunal embodiments of FIGS. 10 and 11. Other specific applications of the principles and teachings of the present invention for securing various types of percutaneous devices at various locations of a patient's body will be apparent to those of skill in the art.

Figure 1:
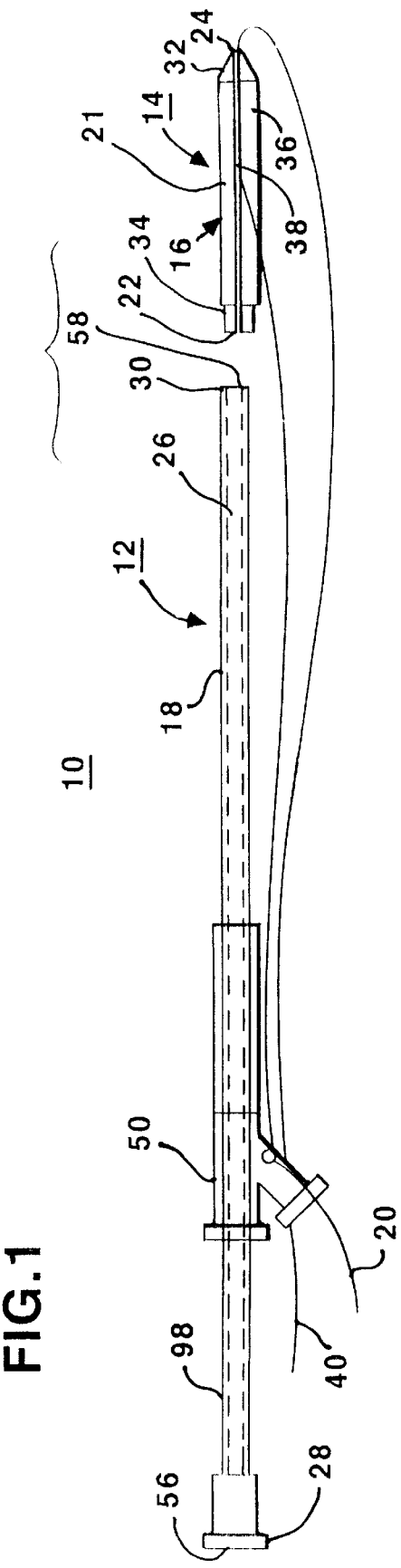
FIG. 1 is a side plan view of the assembly of a percutaneous device and anchor of a preferred embodiment of the present invention with the elongated anchor body separated from the percutaneous device body.
Figure 2:
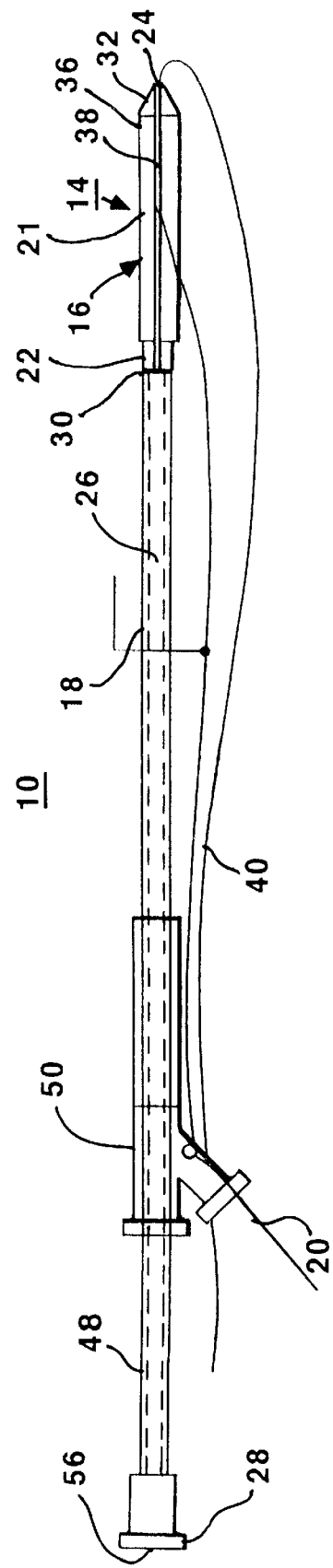
FIG. 2 is a side plan view of a percutaneous device and anchor of a preferred embodiment of the present invention with the elongated anchor body supported by the percutaneous device body for insertion through a surgically prepared percutaneous passageway.
Figure 3:
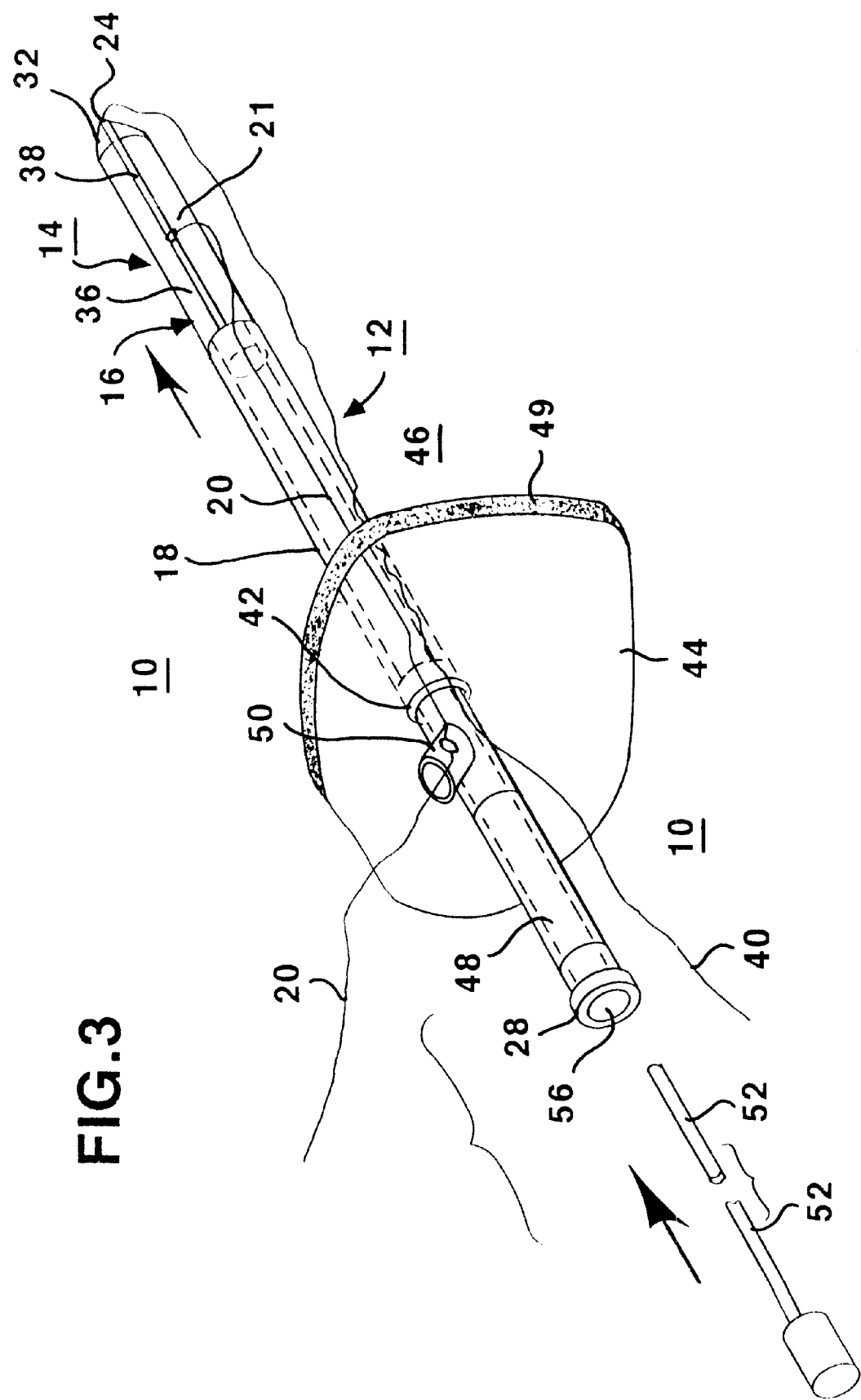
FIG. 3 is a perspective view of the insertion of the assembly of FIG. 1 through a percutaneous passageway to a subcutaneous site of a patient's body.
Figure 4:
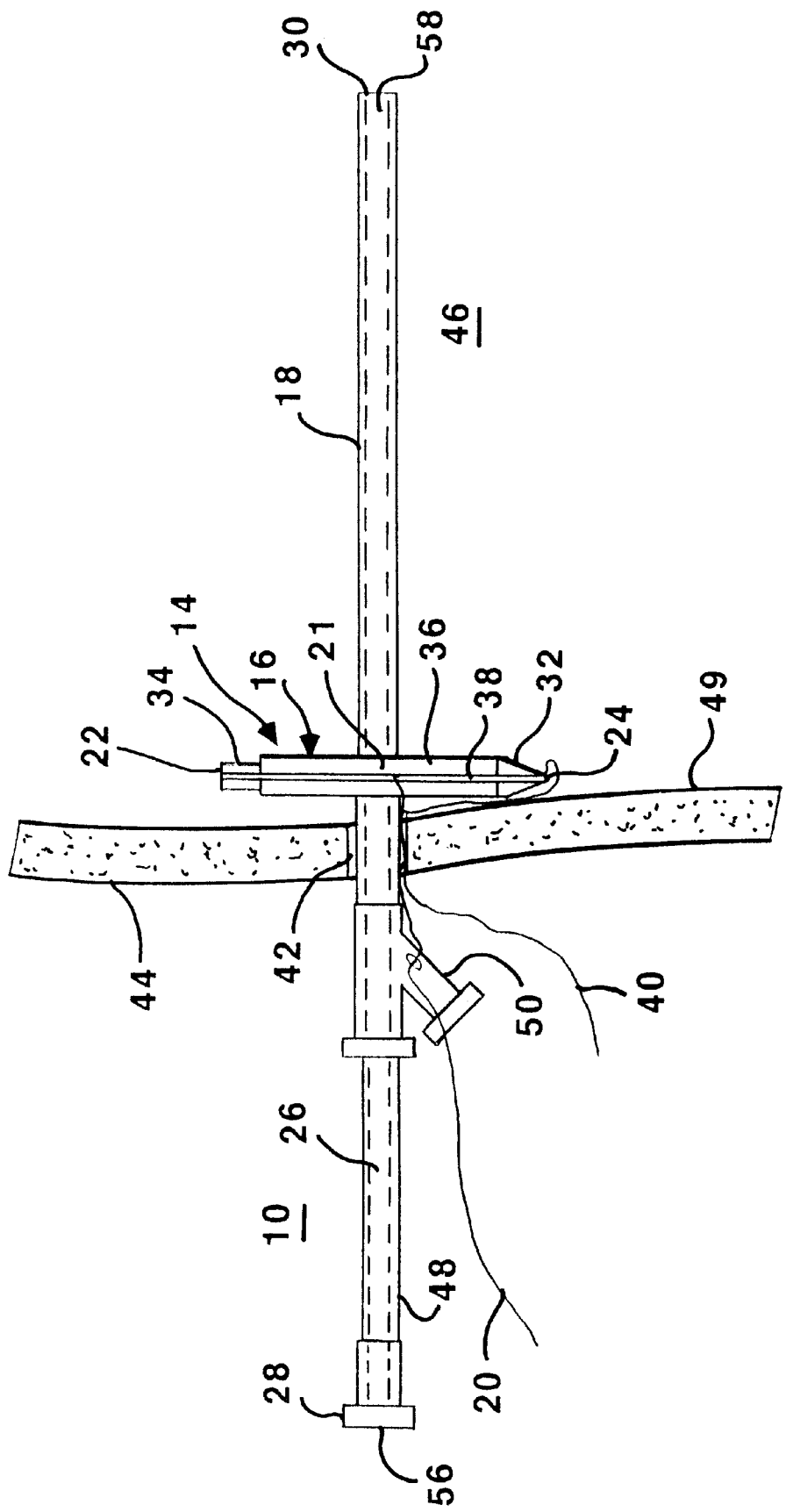
FIG. 4 is a side view of the fixation of the percutaneous device of FIG. 1 in respect to the percutaneous passageway employing the deployed anchor with the anchor body extending across the percutaneous passageway to inhibit advancement or retraction of the percutaneous device body through the percutaneous passageway.

A side plan view of the percutaneous assembly 10 of a percutaneous device 12 and anchor 14 of a preferred embodiment of the present invention with the elongated anchor body 16 separated from the percutaneous device body 18 is shown in FIG. 1. The elongated anchor body 16 supported by the percutaneous device body 18 for insertion through a surgically prepared percutaneous passageway is shown in FIG. 2. The implantable anchor 14 further preferably comprises an elongated, flexible, tensioning filament 20 attached to the elongated anchor body 16 midway between the anchor body proximal end 22 and the anchor body distal end 24, e.g., by insert molding the tensioning filament distal end with the anchor body 16. The anchor body 16 is supported by the percutaneous device body 18 during insertion through the percutaneous passageway as illustrated in FIG. 3 so that the anchor body distal end tapered section 32 extends distally to aid in insertion through a narrow percutaneous passageway. The anchor body 16 is released from and is independent of the percutaneous device body 18 when used as depicted in FIG. 4.

The percutaneous device body 18 comprises one of the above described catheter bodies, tube bodies, or lead bodies, or the like, that are relatively flexible, so that the percutaneous device body 18 can be easily advanced through a percutaneous passageway. Such a percutaneous device body is also formed with a hollow percutaneous device lumen 26 extending from a percutaneous device proximal end 28 of a proximal end fitting 48 to a percutaneous device distal end 30. Proximal end fitting 48 may include a closure element for closing the proximal end opening of the percutaneous device lumen 26 when the percutaneous device 12 is not being employed. The percutaneous device lumen 26 extends between a lumen proximal end opening 56 and a distal lumen end opening 58 and can receive a stylet or guidewire introduced into proximal lumen end opening 56. The stylet or guidewire (shown in reference to the embodiment of FIGS. 5–8) that facilitates advancement of the percutaneous device body 18 through the percutaneous passageway to locate the percutaneous device distal end 30 at desired body site including in a subcutaneous location, e.g., the peritoneal cavity or a surgically created cavity, or in to further body cavities, lumens or tracts, or the like. Moreover, the percutaneous device lumen 26 facilitates the infusion of therapeutic or diagnostic or nutrient fluids therethrough and into the desired body site or the drainage of body fluids from the desired body site. The percutaneous device proximal end 28 is preferably formed with a standard fitting coupled with the percutaneous device lumen 26 for attachment to other devices or tubes or the like, e.g., a conventional female luer fitting, to facilitate such infusion or drainage.

The percutaneous device body 18 is preferably relatively flexible and formed of a variety of materials having a hardness in the range from 30 Shore A to 72 Shore D, for example. Exemplary materials include polyamide polyether block amides (PEBA), polyurethanes, silicone rubbers, nylons, polyethylenes, fluorinated hydrocarbon polymers, and the like.

The anchor body 16 has a generally tubular anchor body outer wall 36 extending between the anchor body distal end tapered section 32 and a stepped down diameter section 34 of the anchor body proximal end 22. The anchor body 16 is preferably formed of a harder durometer material than the material of the percutaneous device body 18 and is more rigid through its length than a comparable length of the percutaneous device body 18. The overall length of the anchor body 16 is preferably about at least three times the diameter of the percutaneous device body 18. For example, the anchor body 16 is preferably 3.0 cm long if the percutaneous passageway and the percutaneous device body are about 1.0 cm in diameter.

The rigidity and length of the anchor body 16, coupled with the strength of the tensioning filament 20 and/or its attachment to the anchor body provides enhanced resistance to accidental retraction of the percutaneous device body 18 through the percutaneous passageway. Preferably the tensioning filament 20 is a 20 pound test filament of braided Dacron or silk, and its attachment 21 with the anchor body 16 resists detachment when a force of up to 20 pounds is applied between them.

Moreover, the anchor body 16 is also preferably formed of a material that is resistant to degradation due to exposure to body fluids, e.g., gastric acid and is filled with radiopaque material to aid in viewing its location at the desired body site. For example, the anchor body can be formed of a relatively hard durometer polymer material filled with a radiopaque material. A radiopaque powder is preferably blended with the polymer material is employed to form the relatively rigid elongated anchor body. Such radiopaque powders include tungsten, tungsten dioxide, tungsten trioxide, barium sulfate, bismuth trioxide, stainless steel, silver iodide, or iodinated organic compounds and others known in the art.

The elongated anchor body 16 also preferably has an elongated guidewire groove 38 formed in the anchor body outer wall 36 that extends between the tapered anchor body distal end 32 and the reduced diameter section 34 of anchor body proximal end 22. A guidewire or stylet (shown in reference to the embodiment of FIGS. 5–8) can be extended through the percutaneous device lumen 26 and through the guidewire groove 38 when the anchor body 16 is assembled to the percutaneous device distal end 30 to aid in advancement through a percutaneous passageway and through any body vessels or cavities. The guidewire can be extended distally from the anchor body 16 any distance that may be found desirable.

Where the anchor body 16 cannot be left in place, a withdrawal filament 40 is optionally coupled to the anchor body distal end tapered section 32, e.g., by molding its end into the anchor body 16, and extended through the percutaneous passageway alongside the percutaneous device body 18 in its use. The withdrawal filament 40 enables axial alignment of the anchor body distal end tapered section 32 to the percutaneous passageway and withdrawal of the anchor body 16 through the percutaneous passageway after use of the percutaneous vice 10 is finished.

An attachment mechanism 50 of the percutaneous device body 18 is schematically depicted in FIGS. 1–11 and is adapted to be located adjacent to the patient's skin for receiving and securing the tensioning filament 20 to the percutaneous device body 18. When the attachment is made, the pull strength of the assembly, that is the resistance to withdrawal of the percutaneous device body 18 and the transversely deployed anchor body 16 largely depends upon the filament strength and/or the strength of the attachment of the filament distal end to the anchor body 16 at its mid-point 21. The transversely deployed anchor body 16 simply cannot be retracted into the percutaneous passageway without causing pain and trauma. As noted above, the combined filament strength and strength of attachment is preferably set to about 20 pounds, so that a force in excess of about 20 pounds applied, either intentionally or accidentally, to the percutaneous device body proximal end can cause the filament 20 or its attachment point 21 to break. This 20 pound pull strength avoids unduly stressing the patient's body, but ensures that the attachment will be maintained under ordinary circumstances. It may be found in practice that this pull strength can be raised or lowered to meet the demands of any particular application of the invention.

Figure 13:
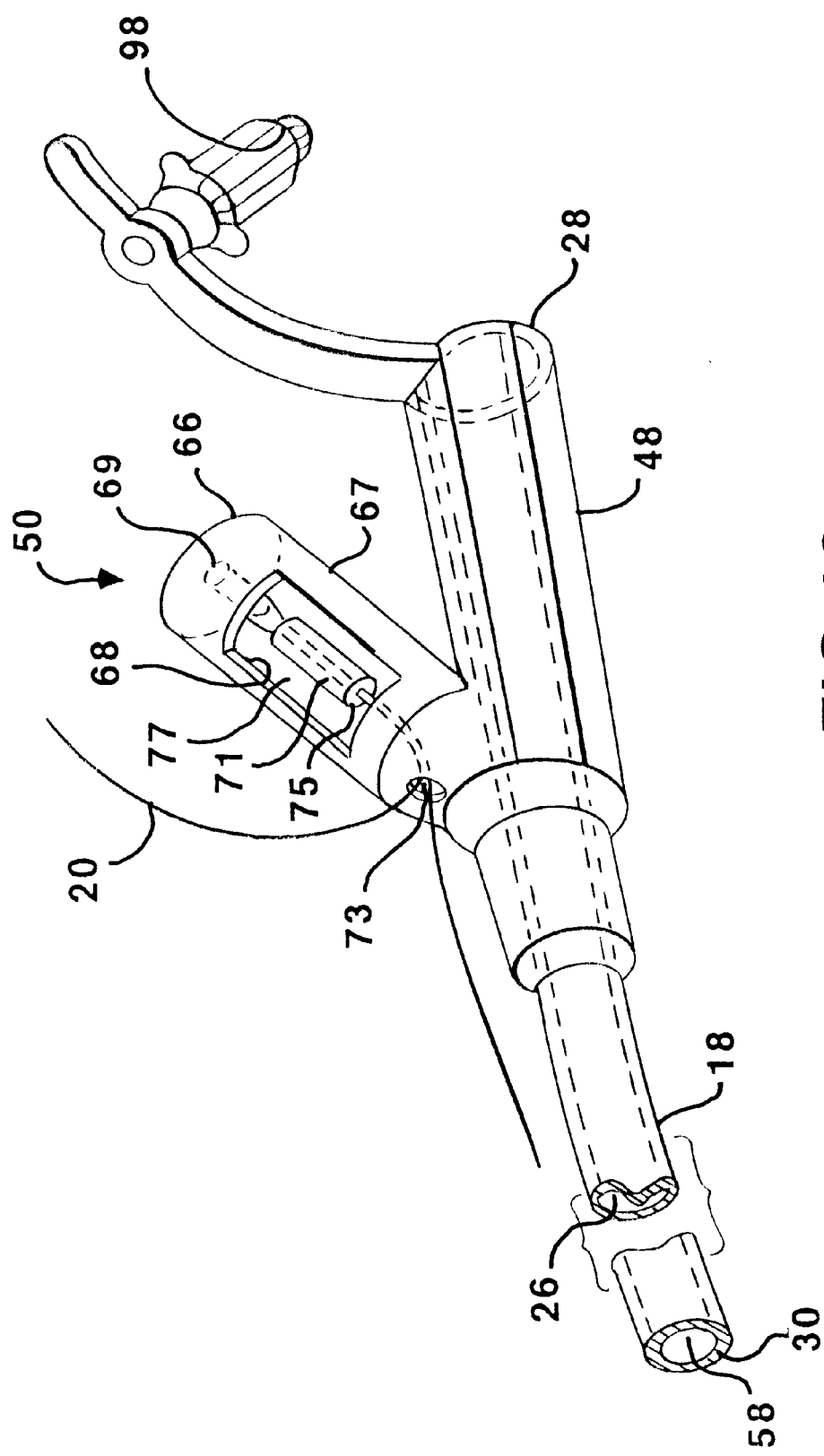
FIG. 13 is a detailed view of one preferred form of an attachment mechanism that can be employed to attach the proximal end of the tensioning filament to the percutaneous device body exterior to the skin.

It will be understood that the attachment mechanism 50 can take a variety of forms, but a preferred embodiment of an attachment mechanism is illustrated in FIG. 13. In this preferred embodiment, a side arm 66 is fixed to the percutaneous device body 18 at some convenient point distal to the proximal end fitting 48 where in use it will bear against the skin 44 adjacent to the percutaneous passageway 42. A ring-shaped, collar or stop can be provided (not shown) that extends outward of the percutaneous device body 18 adjacent to the side arm 66 and bears against the patient's skin adjacent to and covering the percutaneous passageway 42 and to distribute the load applied to the skin 44 in the manner described in the above-incorporated '901 patent, for example. All of the percutaneous device body 18 distal to the side arm is inserted through the percutaneous passageway 42 and into the subcutaneous location 46.

As shown in FIG. 13, an access window 68 is formed in the tubular side arm wall 67 of the side arm 66 exposing the side arm cavity 77 and providing access to a crimp sleeve 71 located therein. A slip pin 69 extends across the side arm cavity 77 and is affixed at its opposite ends to the side arm wall 67. The free end of the side arm 66 can be closed by a cap or left open. The proximal portion of the tensioning filament 20 passes in the proximal direction through a tensioning line feed opening 73 at the base of the side arm 66, through the side arm cavity 77, through the crimp sleeve lumen 75, and is looped around the slip pin 69. Then, the proximal portion of the tensioning filament is passed in the distal direction back through the crimp sleeve lumen 75 and out of the tensioning line feed opening 20.

In the final steps of the procedures described below, the proximal end of the tensioning filament 20 is manually drawn through the crimp sleeve 71 to take up slack and snug the elongated tubular anchor body 16 against the subcutaneous body tissue extending laterally to the percutaneous device body 18 and bridging the percutaneous passageway. Then, the physician employs a tool, e.g., a forceps, extended through the access window 68 to grasp and crush the crimp sleeve 71 against the tensioning filament 20 passing through the crimp sleeve lumen 75 to crush the crimp sleeve 71 against it to thereby prevent movement of the tensioning filament and maintain the applied tension and relationship of the anchor body 16 to the attachment mechanism 50.

FIGS. 3 and 4 are intended to depict a generic practice of the invention extending the elongated percutaneous device body 18 through a percutaneous passageway 42 formed through the skin 44 of a patient's body to locate the percutaneous body distal end 16 at a desired subcutaneous site 46 of the patient's body and for fixing the percutaneous device body 18 at its point of percutaneous insertion through the percutaneous passageway 42. The percutaneous passageway 42 can be surgically created or can be a natural body tract, and the subcutaneous site 42 can be surgically created or be a naturally occurring body cavity or organ cavity or lumen. The subcutaneous site 46 has subcutaneous body tissue 49, e.g., a body organ interior wall, that the anchor 14 can be applied against extending laterally or perpendicularly to the percutaneous device body 18 and bridging the percutaneous passageway as depicted in FIG. 4.

FIG. 3 depicts the assembly 10 being inserted through the percutaneous passageway 42 in the skin 44 with the tensioning filament 20 and withdrawal filament 40 extending alongside the elongated percutaneous device body 18. The anchor body 16 is maintained axially in alignment with the elongated axis of the elongated percutaneous device body 18 and extending distally from its distal attachment to the percutaneous device distal end 30 during introduction through the percutaneous passageway 42. The tensioning filament 20 and the withdrawal filament 40 (if present) extend proximally alongside the percutaneous device body 18 so that the free ends of the tensioning filament 20 and the withdrawal filament 40 trail behind the advanced anchor body and extend through the percutaneous passageway 42 outside the patient's body.

The diameter of the tubular anchor body 16 is approximately the same as the diameter of the tubular percutaneous device body 18, and it is unnecessary to introduce the assembly 10 through the percutaneous passageway employing an introducer having a larger diameter. Consequently, the percutaneous passageway 42 is not dilated beyond the diameter necessary to pass the assembly 10. The anchor body distal end tapered section 32 facilitates expansion of the percutaneous passageway 42 if its opening diameter is less than the diameter of the percutaneous device body 18.

As shown in FIG. 4, when the anchor body 16 is located distal to the subcutaneous body tissue 49 it is to be anchored against, it is released from the percutaneous device distal end 30. The orientation of the released anchor body 16 is changed to be transverse to and to extend laterally across the percutaneous passageway 42 in contact with subcutaneous tissue 49 surrounding the percutaneous passageway 42 by retraction of the tensioning filament 20. The tensioning filament 20 is then attached to the attachment mechanism 50. The length of the anchor body 16 exceeds the width of the percutaneous passageway 42, and the tensioning filament 20 maintains it centered and extending across the percutaneous passageway 42. The deployed anchor body 16 extending transverse to the percutaneous device body 18 and the percutaneous passageway 42 inhibits advancement or retraction of the percutaneous device body 18 through the percutaneous passageway 42.

A number of mechanisms can be employed to release the stepped down section 34 of the anchor body proximal end 22 from the percutaneous device lumen 26 at the distal end opening thereof. In FIG. 3, the short proximal anchor body section 34 is sized in diameter to fit snugly within the distal end opening of the percutaneous device lumen 26. The proximal anchor body end could also be shaped to fit over the percutaneous device distal end 30 or the mating ends could otherwise be configured to fit together until pushed apart. A pusher 52 is advanced into the percutaneous device lumen 26 at the percutaneous device proximal end 28. The pusher 52 is advanced distally within the percutaneous device lumen 26 (optionally over a guidewire extending through the percutaneous device lumen 26 and the groove 38) to push the short proximal anchor body section 34 out of the lumen distal end opening 58 (FIG. 1) of the percutaneous device lumen 26.

Figure 5:
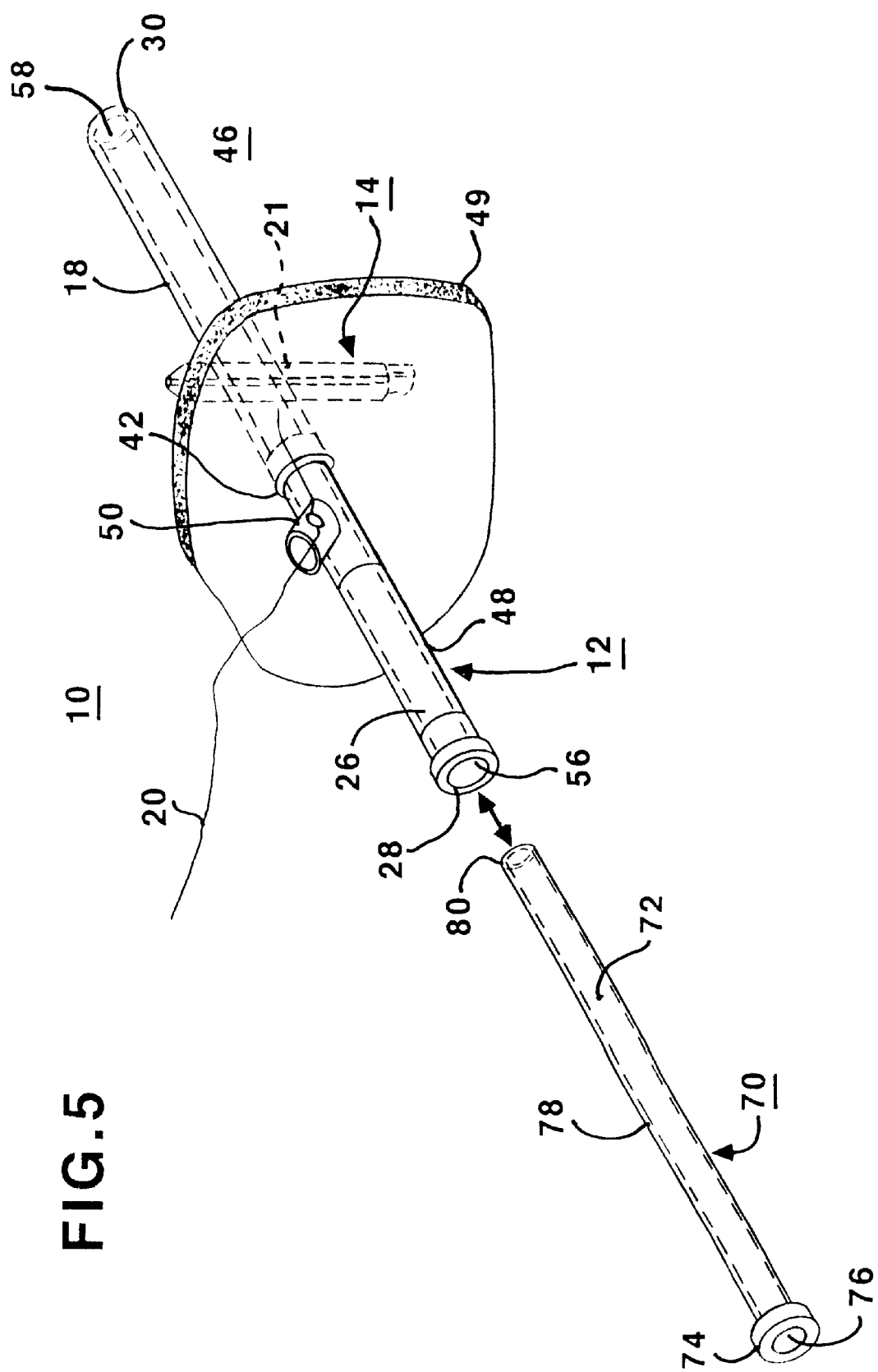
FIG. 5 is a perspective view illustrating the removal and insertion of a disposable inner liner out of and into the percutaneous body lumen in chronic use of a percutaneous device fixed in place by a deployed anchor in accordance with a further aspect of the invention.

FIG. 5 is a perspective view illustrating the removal and insertion of a disposable inner liner 70 out of and into the percutaneous body lumen 26 in chronic use of a percutaneous device 12 fixed in place by a deployed anchor 14 in the manner described above. As noted above, the catheter lumen can become clogged over weeks or months of usage, and it is inconvenient or not possible to clean it. Consequently, it may be necessary to replace the percutaneous device 12 which is costly and may require hospitalization of the patient. To solve this problem, a removable and disposable, tubular, inner liner 70 is formed of an elongated, tubular, liner body 72 enclosing an inner liner lumen 76 that extends between liner lumen end openings at the liner proximal end 74 and the liner distal end 80. The liner outer surface 78 has a diameter that fits within the percutaneous device lumen 26 and a side wall thickness that does not unduly obstruct the percutaneous device lumen 26. The inner liner 70 is formed of a biocompatible material resistant to gastric acids that has a minimal side wall thickness that is sufficient in column strength to the tubular liner body 72 to be pushed distally through the percutaneous device lumen 26. The tubular liner body 72 has a length that corresponds to and is no longer than the length of the percutaneous device lumen 26.

The inner liner 70 can be advantageously employed in any gastrostomy or jejunostomy or gastro-jejunal tube or catheter in order to overcome the problem of clogging of the percutaneous device lumen 26 that occurs in chronic use. When a disposable inner liner 70 becomes clogged, it is simply withdrawn proximal through the lumen proximal end opening, and a new, sterile, inner liner is inserted therethrough and advanced distally until the enlarged liner proximal end 74 abuts the enlarged percutaneous device proximal end 28. This replacement can be accomplished by a physician's assistant or a nurse on an out-patient basis, thereby reducing cost and inconvenience to the patient.

In the gastrostomy and jejunostomy applications depicted in FIGS. 6–9, the assembly 10 comprises a gastrostomy or jejunostomy tube or catheter employing the anchoring system and method of the present invention. The assembly 10 preferably includes the disposable and replaceable inner liner 70 and incorporates further mechanism for attaching and detaching the anchor body proximal end reduced diameter section 34 to the percutaneous device distal end 30. To simplify the following description the common components of the percutaneous assembly 10 that have been described above are alternatively referred to in reference to these figures employing the term "gastrostomy catheter" which is intended to embrace both the gastrostomy and jejunostomy embodiments.

In FIGS. 6–9, the gastrostomy/jejunostomy application is depicted wherein a stoma tract 64 is formed between the stomach wall 62 and the skin 44 through the intervening subcutaneous abdominal wall and tissue layers. The stoma tract 64 can be effected in a field that is previously surgically prepared using a plurality of T-fasteners to draw the skin 44, underlying abdominal wall and subcutaneous tissue layers, and stomach wall 62 together in the manner described in the above-incorporated '040, '086, and '583 patents to avoid leakage of stomach fluids into subcutaneous body tissue and cavities. Then, the procedure and system or the present invention can be used to locate the gastrostomy catheter distal end 30 and the anchor body 16 inside the stomach cavity 60 to enable release of the anchor 14 therein. In this case, the anchor body 16 is drawn against the stomach wall 62, and the tensioning filament 20 is coupled with the attachment mechanism 50 located outside the stoma tract 64 and adjacent to or bearing against the patient's skin 44. In these embodiments of the invention, the gastrostomy catheter body 18 can be a tube of about 0.6 cm in outer diameter about 30 cm long for accessing the stomach cavity 60 or about 60 cm long for accessing the small intestine. The gastrostomy catheter body 18 can be formed of wide variety of bio-compatible plastic materials listed above. The proximal gastrostomy catheter end can be formed with a cap that can be closed to admit infused fluids through the liner lumen 76 and closed at other times of the type depicted in the above-incorporated '529 patent, for example.

Although the above described approach of fixing the anchor body proximal end 22 to the gastrostomy catheter body distal end 30 in axial alignment to the gastrostomy catheter body 18 and using the pusher 52 to release it into the stomach cavity can be used, a further approach is preferred that also advantageously enhances the chronic use of the gastrostomy catheter and anchor assembly 10.

Figure 7:
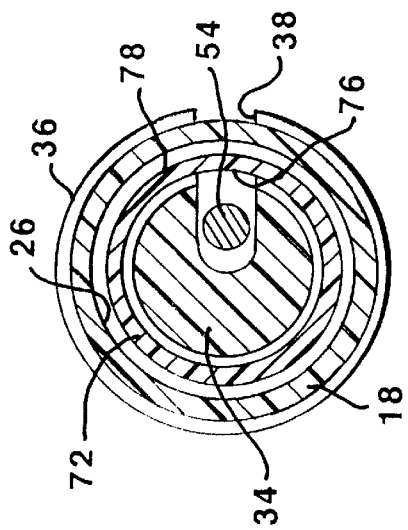
FIG. 7 is an end cross-section view taken along lines 7—7 of FIG. 6 showing the engagement of the anchor body proximal end with the disposable inner liner distal end.

The diameter of the tubular anchor body outer wall 36 is sized to be approximately the same or slightly larger than the outer diameter of the tubular gastrostomy catheter body 18. The outer diameter of the tubular anchor body outer wall 36 is shown as being slightly larger in diameter in FIGS. 6–9 and exaggerated in FIG. 7 for ease of illustrating the abutment of the anchor body outer wall 36 against the catheter body distal end 30 and the tight fitting of the short proximal section 34 of the anchor body 16 within the liner lumen 76. The anchor body 16 is therefore supported at the distal end of the assembled tubular outer gastrostomy catheter body 18 and the inner liner 70 with the short proximal section 34 of the anchor body 16 snugly fitted within the distal end opening of the liner lumen 76. The guidewire 54 extends through the groove 38, including that portion extending along the proximal section 34, as shown in FIG. 7.

Figure 6:
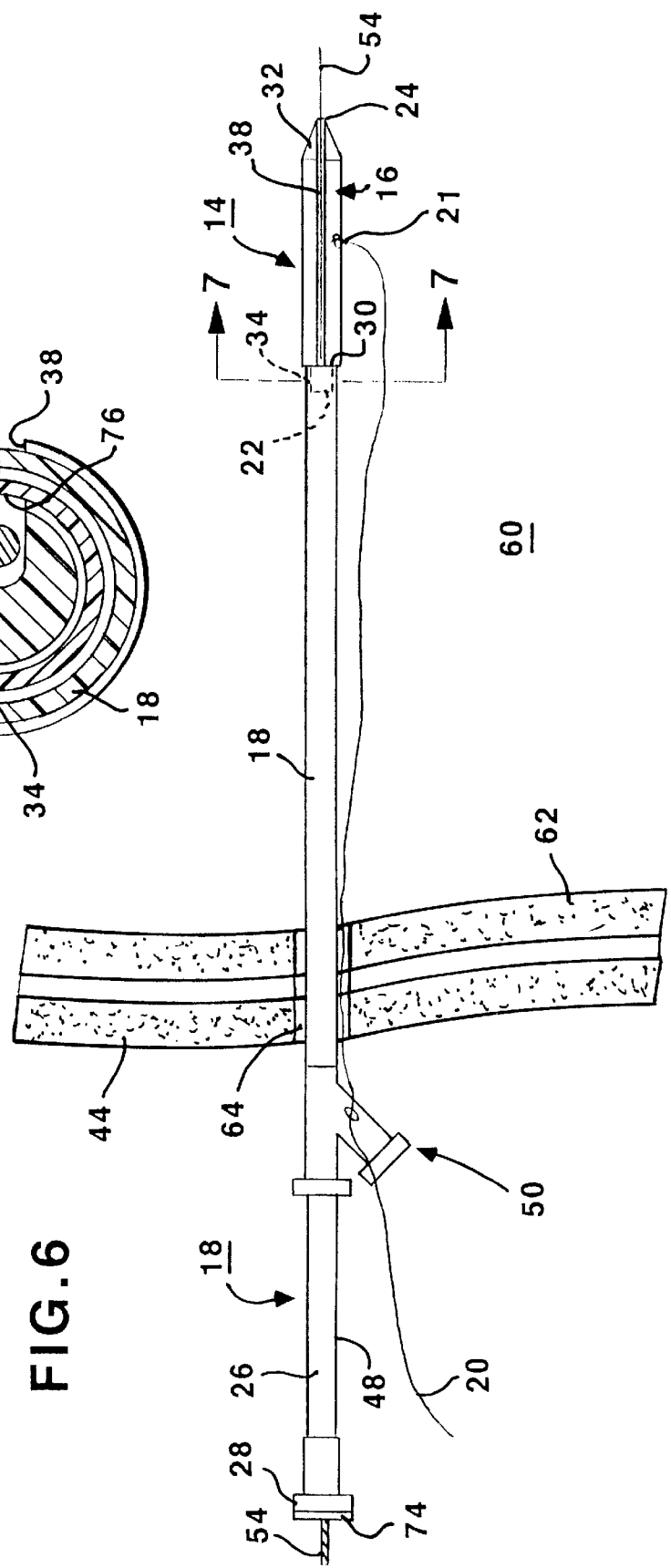
FIG. 6 is a side plan view of the assembly of a gastrostomy or jejunostomy tube employing the disposable inner liner and anchor of a preferred embodiment of the present invention with the elongated anchor body supported at the distal end by the inner liner distal end and axially aligned with the gastrostomy catheter body and inserted over a previously placed guidewire through a surgically prepared stoma tract.

In FIG. 6, after the anchor body 16 is inserted through the stoma tract 64 into the stomach cavity 60, optionally over the guidewire 54 previously inserted through the stoma tract 64, the liner body 72 is retracted to the retracted position shown in FIG. 8. The proximal retraction withdraws the liner lumen 76 from embracing the short proximal section 34 of the anchor body 16, allowing the anchor body 16 to float freely out of the catheter body lumen 26 and into the stomach cavity 60. As can be seen in FIG. 7, the diameter of the catheter body lumen 26 is sufficiently larger than the outer diameter of the short proximal section 34 that it cannot restrain release of the anchor body 16.

Then, the inner liner 70 is advanced back to the fully inserted position, and the released anchor body 16 is drawn toward the stomach wall 62 by retraction of the tensioning filament 20, as depicted in FIG. 9. The anchor body 16 pivots about the attachment point 21 of the tensioning filament 20 to the anchor body 16 and extends laterally to the gastrostomy catheter body 18 and bridging across the stoma tract 64 as illustrated in FIG. 9. The tensioning filament 20 extending outside the stoma tract 64 is then fixed to the attachment mechanism 50 in the manner described above.

FIGS. 10 and 11 are views of alternate embodiments of two lumen, gastro-jejunal tube or catheter assemblies 82 and 182, which incorporate both a gastrostomy catheter and a jejunostomy catheter in the same percutaneous assembly incorporating the fixation system and method of the present invention. In the following discussion, the components of the above-described embodiments that are common with these embodiments retain the same parts numbers. The common components comprise the percutaneous device 12 employed to form the jejunostomy catheter, and also include the removable inner liner 70, the guidewire 54 and the anchor 12. The common components are referred to as "jejunostomy catheter" components in this embodiment. The gastrostomy catheter components are numbered separately.

The depicted gastro-jejunal tube assembly 82 of FIG. 10 is of a co-axial design of the type disclosed in the above-referenced '901 patent having a relatively short, outer gastrostomy catheter body 84 containing an outer catheter lumen 86 through which the relatively long inner jejunostomy catheter body 18 extends. The outer co-axial catheter lumen 86 extends from its annular distal end opening 88 proximally to a manifold Y-connector coupling the annular gastrostomy catheter lumen 86 with a gastrostomy catheter proximal end fitting 92. A gastrostomy catheter fitting lumen 94 of fitting 92 is thereby in fluid communication with the gastrostomy catheter lumen 86. The fitting 92 supports a gastrostomy catheter fitting closure flap and plug 98 that can be bent and fitted into the end opening of the gastrostomy catheter fitting lumen 94 to close it when it is not in use. The proximal end opening of the gastrostomy catheter fitting lumen 94 can be coupled with a suction pump to aspirate stomach contents or to a source of nutrients for receiving infused nutrients in the manner depicted in the '901 patent. The nutrients are transmitted through the outer catheter lumen 86 in the annular space surrounding the jejunostomy catheter body 18 therein and emitted through the annular end opening 88 and side openings 90, if provided.

In this embodiment, the inner liner 70 is preferably disposed within the jejunostomy catheter lumen 26 as described above in reference to FIG. 5. The jejunostomy catheter body 18 is of a length that allows its distal end 30 to be extended through the outer catheter lumen 86, through the stomach cavity, and then into the small intestine over a previously positioned guidewire 54 traversing the inner liner lumen. Nutrients can also be infused from the jejunostomy catheter proximal end 28 through the jejunostomy catheter proximal end fitting 48 and the jejunostomy catheter lumen 26 and emitted from the lumen end opening at the jejunostomy catheter distal end 30 into the small intestine.

In this co-axial gastro-jejunal catheter assembly 82, the anchor 14 is supported at the jejunostomy catheter distal end 30 in cooperation with the liner distal end 80 and the guidewire 54 in the manner described above with respect to FIGS. 6–8. The anchor 14 is released in the manner depicted in of FIG. 8 when the jejunostomy catheter distal end 30 and anchor 14 are introduced into the stomach cavity. Then, the jejunostomy catheter distal end 30 is advanced into the small intestine over the guidewire 54. The anchor 14 is released, retracted and fixed against the stomach wall bridging the stoma as shown in FIG. 8 and as described above.

In the side-by-side, gastro-jejunal catheter embodiment depicted in FIG. 11, the long jejunostomy catheter body 18 and the shorter, gastrostomy catheter body 100 are mounted in a side-by-side arrangement. The gastrostomy catheter proximal fitting 92 and the jejunostomy catheter proximal end fitting 48 are configured with closure elements as described above in reference to FIG. 10. In this embodiment, the side-by-side, long jejunostomy catheter lumen 26 and the shorter, gastrostomy catheter lumen 102 are both capable of receiving a replaceable liner 70 and 70', respectively. Therefore, the long jejunostomy catheter distal end 30 and the shorter gastrostomy catheter lumen 104 both can support an anchor 14 in the manner depicted in FIGS. 6–8 and described above. Or both catheters can be used to support and release two such anchors 14. Again, the anchor(s) 14 is supported by the liner lumen 76 at the liner lumen distal end 80 during introduction through the stoma tract until it is located within the stomach cavity as shown in FIG. 7. Then the liner 70 is retracted to release the anchor body 16 as shown in FIG. 8, and the tensioning filament 20 is retracted to lodge the anchor body 16 against the stomach wall where it is fixed in place in the manner shown in FIG. 9 and described above.

Figure 12:
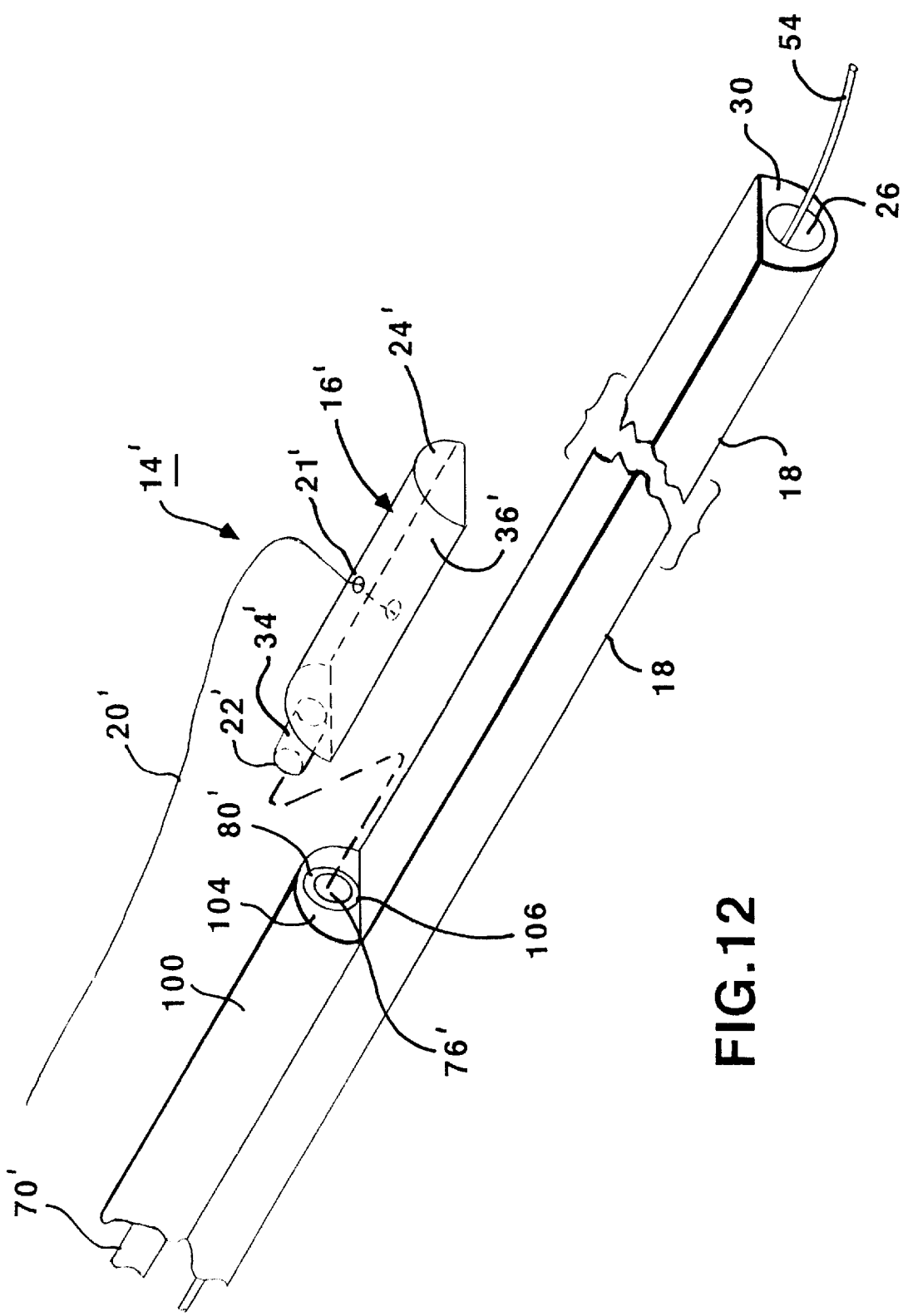
FIG. 12 is a partial perspective view of an alternative form of the anchor body adapted to be positioned at the distal end of the gastrostomy tube of the two lumen, side-by-side, gastro-jejunal tube or catheter of FIG. 11.

FIG. 12 is a partial perspective view of an alternative form of the anchor body 16' adapted to be positioned at the gastrostomy catheter distal end 104 of the two lumen, side-by-side, gastro-jejunal tube or catheter of FIG. 11. The anchor body 16' has an outer wall 36' that is shaped in a somewhat hemispheric manner between the anchor body proximal and distal ends 22' and 24' to generally conform to the shape of the gastrostomy catheter body 100 and the distally extending flattened portion of the jejunostomy catheter body 18. The guidewire 54 is extended through the gastrostomy catheter lumen 26, so there is no need for a guidewire accommodating groove extending along the length of the anchor body 16'. Preferably, the reduced diameter section 34' of the anchor body proximal end 22' is inserted into the liner lumen 76' at the liner distal end 80' of the liner 70' and supported frictionally therein in the manner described above with reference to FIG. 6 during introduction through the stoma tract until the anchor body 16' is located within the stomach cavity as shown in FIG. 7. Then the liner 70' is retracted to release the anchor body 16' in the manner shown in FIG. 8 with respect to anchor body 16. The tensioning filament 20' is then retracted to lodge the anchor body 16' against the stomach wall where it is fixed in place in the manner shown in FIG. 9 and described above.

In these gastrostomy and jejunostomy applications, a withdrawal filament 40 of the type illustrated in FIGS. 1–5 could be employed for withdrawing the anchor body 16, 16' through the stoma tract 64, but it may not be necessary. The anchor body 16, 16' is preferably molded of an inert, bio-compatible plastic material and is about 0.6 cm in diameter and about 4.0 cm long. Because of its length and diameter, the anchor body 16, 16' can be passed through the intestinal system of the patient. Therefore, when the gastrostomy or jejunostomy or gastro-jejunal catheter is to be withdrawn from the stoma tract 64, it is only necessary to sever the tensioning filament 20, allowing the anchor body 16, 16' to be passed through the digestive system.

One preferred coupling and release means extending the length of the percutaneous device body 18 that frictionally engages a coupling member or feature of the anchor body 16, 16' to hold it against and extending distally from the percutaneous device distal end 30 employs the disposable inner liner 70, 70' as shown in FIGS. 6 and 7 that allows release of the anchor body 16 as shown in FIGS. 8 and 9. Equivalent coupling elements could be substituted for these elements that also rely upon frictional engagement of the proximal end of the anchor body 16, 16' with the distal end of an engaging and release member extending the length of the percutaneous device body 18 that can be manipulated at the proximal end to overcome the frictional engagement and to release the anchor body 16, 16'. For example, an elongated rod or wire or filament could be fitted, e.g., by molding or friction fitting its distal end into a bore into or about a feature of the anchor body proximal end 22, 22', thereby forming a junction therewith that is separable by applied force. The elongated rod or wire or filament is then extended either alongside the gastrostomy catheter body 18 through the percutaneous passageway or within the percutaneous device lumen 26 extending through the percutaneous passageway. After placement of the anchor body 16, 16' is achieved as shown in FIGS. 3 and 6, retraction force can be applied to the proximal end of the elongated rod or wire or filament that exceeds the retention force at the junction thereby releasing the anchor body 16, 16' in the manner illustrated in FIGS. 1 or 8, for example. This approach would be of particular use where the available lumen of the percutaneous device body is relatively small in diameter.

The attachment mechanism 50 can take other forms e.g., a collar that is fixed or is movable along the percutaneous body and fixed against a proximal stop when the slack is taken out of the tensioning filament. The crimp sleeve or an equivalent clamp can be formed as part of the collar. The percutaneous device body and the anchor are inserted through the percutaneous passageway with the tensioning filament and withdrawal filament (if present) trailing alongside and extending outside the body until the distal end of the percutaneous device is positioned at the intended subcutaneous location. The percutaneous device is adjusted or the collar is along the percutaneous device body until, in either case, it is located adjacent to the patient's skin. The tensioning filament is then tensioned to take up slack and snug the elongated tubular anchor body against the subcutaneous tissue and across the percutaneous passageway. The crimp or clamp is closed to clamp the tensioning filament extending through the percutaneous passageway alongside the percutaneous device body to the percutaneous device body.

The anchor body 16, 16' is depicted as generally tubular having a width corresponding to the tubular anchor body diameter that is smaller than the anchor body length, but it will be realized that it need not be tubular and can have other cross-section shapes that inhibit retraction when the anchor body is deployed transversely or laterally across and bridging the percutaneous passageway that the percutaneous device extends through. For example, the anchor body 16, 16' may be square or rectangular or plate like and have an anchor body width that allows passage through the percutaneous passageway and is less than the anchor body length.

Moreover, it will be understood that alternative shapes of the anchor body could be devised to accommodate its temporary attachment alongside or surrounding a distal segment of the percutaneous device body during percutaneous insertion through the passageway and released from it at the desired body site and deployed in the manner depicted in FIG. 4. For example, the anchor body could be a tube or a tube half section mounted about the distal end of the catheter body and ejected therefrom when the assembly is inserted through the percutaneous passageway. However, such an approach would increase the diameter of the assembly by the thickness of the tubular anchor body unless the catheter body distal end section supporting the anchor body is reduced in diameter to accommodate the thickness.

The above described preferred embodiments of the percutaneous assemblies and methods of the invention provide for the temporary assembly of the anchor onto the percutaneous device, the simultaneous insertion of both through the percutaneous passageway, and the release and deployment of the anchor at the desired body site as depicted in FIG. 4, for example. However, the present invention encompasses any manner of inserting an anchor through the percutaneous passageway, either before, simultaneously with, or after the insertion of the percutaneous device body therethrough and then making the connection of the tensioning filament with the percutaneous device as depicted in FIG. 4.

While the tensioning filament 20, 20' is depicted as extending alongside and outside the percutaneous device body, it could alternatively be extended through a portion of the percutaneous device lumen via appropriately placed side holes through the percutaneous device body wall. The tensioning filament extends through the percutaneous passageway in either approach. The side holes would have to be located to allow positioning of the anchor body against the body tissue as illustrated in FIG. 4, for example, and attachment to the external attachment mechanism.

The methods and assemblies described above can be employed to anchor drainage tubes, electrical leads and any catheters inserted into other body lumens or cavities through a variety of body passageways, including natural ducts, vessels or tracts or surgically created passageways wherever it is possible to locate the anchor body into a cavity to bear against body tissue at a desired body site. In some instances it may be necessary to form a subcutaneous cavity adjacent the skin incision to receive the anchor body, e.g., during the stabilization of an electrical lead or catheter that extends a distance to the desired site in the body.

It will also be apparent that while the present invention is specifically described for use in treatment of a human patient, that its principles and teachings can be applied to animal veterinary care and animal experimental subjects which can be characterized as "patients" in accordance with the invention and the following claims.

Although particular embodiments of the invention have been described herein in some detail, this has been done for the purpose of providing a written description of the invention in an enabling manner and to form a basis for establishing equivalents to structure and method steps not specifically described or listed. It is contemplated by the inventors that the scope of the limitations of the following claims encompasses the described embodiments and equivalents thereto now known and coming into existence during the term of the patent. Thus, it is expected that various changes, alterations, or modifications may be made to the invention as described herein without departing from the spirit and scope of the invention as defined by the appended claims.

PARTS LIST FOR FIGS. 1–12 percutaneous assembly 10
percutaneous device 12
anchor 14, 14'
elongated anchor body 16, 16'
percutaneous device body 18
tensioning filament 20,20'
tensioning filament attachment point 21,21'
anchor body proximal end 22, 22'
anchor body distal end 24,24'
percutaneous device lumen 26
percutaneous device proximal end 28
percutaneous device distal end 30
anchor body distal end tapered section 32 anchor body proximal end reduced diameter section 34,34'
anchor body outer wall 36,36'
elongated guidewire groove 38
withdrawal filament 40
percutaneous passageway 42
skin 44
subcutaneous site 46
proximal end fitting 48
subcutaneous body tissue 49
attachment mechanism 50
pusher 52
guidewire 54
lumen proximal end opening 56
lumen distal end opening 58
stomach cavity 60
stomach wall 62
stoma tract 64
side arm 66
side arm wall 67
access window 68
slip pin 69
disposable inner liner 70,70'
crimp sleeve 71
liner body 72
tensioning line feed opening 73
liner proximal end 74
crimp sleeve lumen 75
liner lumen 76,76'
side arm cavity 77
liner body outer surface 78
liner distal end 80, 80'
gastro-jejunal tube assembly 82, 82'
co-axial gastrostomy catheter body 84
co-axial gastrostomy catheter lumen 86
gastrostomy catheter lumen annular end opening 88
gastrostomy catheter lumen side opening 90
gastrostomy catheter proximal end fitting 92
gastrostomy catheter proximal end opening 94
gastrostomy catheter lumen closure 96
jejunostomy catheter lumen closure 98
side mounted gastrostomy catheter body 100
side mounted gastrostomy catheter lumen 102
side mounted gastrostomy catheter distal end 104
side mounted gastrostomy catheter distal end opening 106

What is claimed is:

1. A percutaneous assembly comprising:
   a percutaneous device having an elongated percutaneous device body adapted to be extended through a percutaneous passageway formed through the skin of a patient's body to locate a percutaneous device distal end at a desired body site of a patient's body; and
   means for fixing the percutaneous device body at its point of percutaneous insertion through the percutaneous passageway to inhibit advancement or retraction of the percutaneous device body through the percutaneous passageway further comprising:
   an implantable anchor adapted to be inserted through the percutaneous passageway and deployed subcutaneously in engagement with body tissue, the implantable anchor comprising an elongated anchor body adapted to be separated from and to extend laterally with respect to and alongside the percutaneous device body and a tensioning filament coupled thereto adapted to be retracted through the percutaneous passageway to draw the deployed anchor body against body tissue and toward the patient's skin; and
   external attachment means secured against the percutaneous device body and adapted to be located adjacent to the patient's skin in use for engaging the tensioning filament so that tension applied therethrough and between the external attachment means and the anchor body inhibits advancement or retraction of the percutaneous device body through the percutaneous passageway.

2. The percutaneous assembly of claim 2, further comprising a withdrawal filament attached to one of the opposed ends of the anchor body adapted to be extended alongside the percutaneous device body extending through the percutaneous passageway whereby retraction of the withdrawal filament aligns the anchor body axially with the percutaneous passageway and withdraws the anchor body axially and proximally through the percutaneous passageway.

3. The percutaneous assembly of claim 1, wherein:
   the elongated percutaneous device body extends between a percutaneous device proximal end and a percutaneous device distal end; and
   the elongated anchor body extends between an anchor body proximal end and an anchor body distal end; and further comprises:
   coupling means for coupling the anchor body proximal end with the percutaneous device distal end for supporting the anchor body in axial alignment with the percutaneous device body during insertion through the percutaneous passageway.

4. The percutaneous assembly of claim 1, wherein:
   the elongated percutaneous device body is generally tubular having a percutaneous body diameter and extends between a percutaneous device proximal end and a percutaneous device distal end; and
   the elongated anchor body extends between an anchor body proximal end and an anchor body distal end and has an anchor body width that is about the same as the percutaneous body diameter; and further comprising:
   coupling means for coupling the anchor body proximal end with the percutaneous device distal end for supporting the anchor body in axial alignment with the percutaneous device body during insertion through the percutaneous passageway.

5. The percutaneous assembly of claim 1, wherein:
   the elongated percutaneous device body extends between a percutaneous device proximal end and a percutaneous device distal end; and
   the elongated anchor body extends between an anchor body proximal end and an anchor body distal end; and further comprising
   coupling means for coupling the anchor body proximal end with the percutaneous body distal end for supporting the anchor body in axial alignment with the percutaneous device body during insertion through the percutaneous passageway; and:
   release means for selectively releasing the coupling means to release the anchor body proximal end from the percutaneous device distal end after insertion through the percutaneous passageway to deploy the anchor body extending against body tissue laterally across the percutaneous passageway and the percutaneous device body.

6. The percutaneous assembly of claim 1, wherein:
   the elongated percutaneous device body extends between a percutaneous device proximal end and a percutaneous device distal end and encloses a percutaneous device lumen extending between percutaneous device lumen end openings at the percutaneous device proximal and distal ends; and the elongated anchor body extends between an anchor body proximal end and an anchor body distal end, the anchor body proximal end extending into the percutaneous device lumen at the percutaneous body distal end for supporting the anchor body in axial alignment with the percutaneous device body during insertion through the percutaneous passageway; and the percutaneous assembly further comprises:

release means extending through the percutaneous device lumen for selectively releasing the anchor body proximal end from the percutaneous device distal end by ejecting the anchor body proximal end from the percutaneous device lumen after insertion through the percutaneous passageway to deploy the anchor body extending against body tissue and laterally across the percutaneous passageway and the percutaneous device body.

7. The percutaneous assembly of claim 1, wherein the elongated percutaneous device body extends between a percutaneous device proximal end and a percutaneous device distal end and encloses a percutaneous device lumen having a percutaneous device lumen diameter and that extends between percutaneous device lumen end openings at the percutaneous device proximal and distal ends, the percutaneous assembly further comprising:

a disposable, tubular, inner liner having a liner lumen and a liner outer diameter sized to fit within the percutaneous device lumen that is adapted to be fitted within the percutaneous device lumen and removed and replaced if the liner lumen becomes obstructed in chronic use.

8. The percutaneous assembly of claim 7, wherein:

the inner liner has a liner body extending between a liner proximal end and a liner distal end and a liner length that allows location of the liner distal end within the percutaneous device lumen at the percutaneous device distal end when the inner liner is fitted within and advanced distally through the percutaneous device lumen;

the elongated anchor body extends between an anchor body proximal end and an anchor body distal end; and the anchor body proximal end extends into the percutaneous device lumen at the percutaneous body distal end for supporting the anchor body in axial alignment with the percutaneous device body during insertion through the percutaneous passageway.

9. The percutaneous assembly of claim 7, wherein:

the inner liner has a liner body extending between a liner proximal end and a liner distal end and a liner length that allows location of the liner distal end within the percutaneous device lumen at the percutaneous device distal end when the inner liner is fitted within and advanced distally through the percutaneous device lumen; and the elongated anchor body extends between an anchor body proximal end and an anchor body distal end; and further comprises:

an anchor body proximal end section extending into the liner lumen for releasably coupling the anchor body proximal end to the liner distal end to support the anchor body in axial alignment with the percutaneous device body during insertion through the percutaneous passageway, whereby, after insertion of the assembly through the percutaneous passageway, the inner liner is adapted to be retracted proximally within the percutaneous device lumen to withdraw the liner distal end from the anchor body proximal end section and to release the anchor body, enabling the anchor body to be retracted and to extend against body tissue and laterally across the percutaneous passageway and the percutaneous device body.

10. The percutaneous assembly of claim 1, adapted to be deployed with a guidewire extending through the percutaneous passageway, wherein:

the elongated percutaneous device body extends between a percutaneous device proximal end and a percutaneous device distal end and encloses a percutaneous device lumen having a percutaneous device lumen diameter that extends between percutaneous device lumen end openings at the percutaneous device proximal and distal ends, the percutaneous device lumen adapted to receive the guidewire extending therethrough, the elongated anchor body extends between an anchor body proximal end and an anchor body distal end and further comprises:

coupling means at the anchor body proximal end extending into the percutaneous device lumen from the percutaneous body distal end for releasably coupling the anchor body proximal end to the percutaneous device distal end to support the anchor body in axial alignment with the percutaneous device body during insertion through the percutaneous passageway; and an elongated channel formed alongside and extending into the anchor body between the anchor body proximal end and the anchor body distal end for receiving the guidewire extending distally from the percutaneous device distal end to allow advancement of the percutaneous assembly of the anchor body extending axially and distally from the percutaneous device distal end over the guidewire.

11. The percutaneous assembly of claim 10, the further comprising:

release means extending through the percutaneous device lumen for selectively releasing the anchor body proximal end from the percutaneous device distal end by ejecting the coupling means from the percutaneous device lumen after insertion of the percutaneous assembly through the percutaneous passageway over the guidewire, the elongated channel allowing the anchor body to laterally separate from the guidewire so that the anchor body can be deployed to extend against body tissue and laterally across the percutaneous passageway and the percutaneous device body by retraction of the tensioning filament.

12. The percutaneous assembly of claim 11, further comprising:

a disposable, tubular, inner liner having a liner lumen adapted to receive the guidewire extending therethrough and a liner outer diameter sized to fit within the percutaneous device lumen that is adapted to be fitted within the percutaneous device lumen and removed and replaced if the liner lumen becomes obstructed in chronic use.

13. The percutaneous assembly of claim 12, wherein:

the inner liner has a liner body extending between a liner proximal end and a liner distal end and a liner length that allows location of the liner distal end within the percutaneous device lumen at the percutaneous device distal end when the inner liner is fitted within and advanced distally through the percutaneous device lumen; and the coupling means at the elongated anchor body proximal end extends into the liner lumen from the percutaneous body distal end for releasably coupling the anchor body proximal end to the liner distal end to support the anchor body in axial alignment with the percutaneous device body and for aligning the elongated channel with the liner lumen to allow the guidewire to extend through the liner lumen and the elongated channel during advancement of the percutaneous assembly over the guidewire and through the percutaneous passageway.

14. The percutaneous assembly of claim 12, wherein:

the inner liner has a liner body extending between a liner proximal end and a liner distal end and a liner length that allows location of the liner distal end within the percutaneous device lumen at the percutaneous device distal end when the inner liner is fitted within and advanced distally through the percutaneous device lumen;

the coupling means at the elongated anchor body proximal end further comprises an anchor body proximal end section extending into the liner lumen for releasably coupling the anchor body proximal end to the liner distal end to support the anchor body in axial alignment with the percutaneous device body and to dispose the elongated channel in alignment with the liner lumen to allow the guidewire to extend through the liner lumen and the elongated channel during advancement of the percutaneous assembly over the guidewire and through the percutaneous passageway; and the release means comprises the inner liner which, upon retraction proximally within the percutaneous device lumen after insertion of the percutaneous assembly through the percutaneous passageway, withdraws the liner distal end from engagement with the anchor body proximal end section and releases the anchor body.

15. The percutaneous assembly of claim 1, wherein:

the elongated percutaneous device body is generally tubular, has a percutaneous body diameter, and extends between a percutaneous device proximal end and a percutaneous device distal end; and the elongated anchor body is generally tubular and extends between an anchor body proximal end and an anchor body distal end and has an anchor body length that exceeds the percutaneous body diameter sufficiently to enable the elongated anchor body to bridge the percutaneous passageway when deployed and tensioned by the tensioning filament.

16. The percutaneous assembly of claim 1, wherein the elongated percutaneous device body extends between a percutaneous device proximal end and a percutaneous device distal end and encloses a percutaneous device lumen extending between lumen end openings at the percutaneous device proximal and distal ends, the percutaneous assembly further comprising:

a tubular inner liner fitted within the percutaneous device lumen having an liner lumen and extending between an liner proximal end and an liner distal end; and wherein:

the elongated anchor body extends between an anchor body proximal end and an anchor body distal end and further comprises a coupling member at the anchor body proximal end adapted to releasably couple the anchor body proximal end to the liner distal end to support the anchor body in axial alignment with the percutaneous device body during insertion through the percutaneous passageway; and the tubular liner is adapted to be moved from the tubular liner proximal end proximally within the percutaneous device lumen from an anchor body engagement position extending between the percutaneous device proximal end and the percutaneous device distal end with the coupling member engaged with the liner distal end and an anchor body release position withdrawing the liner distal end proximally from the percutaneous device distal end and releasing the coupling member of the anchor body.

17. The percutaneous assembly of claim 1, wherein the anchor body is formed with a channel extending between its opposed ends for passage of a stylet or guide wire therethrough.

18. The percutaneous assembly of claim 1, wherein the anchor body is formed of a radiopaque material.

19. The percutaneous assembly of claim 1, wherein:

the elongated percutaneous device body is generally tubular and has a percutaneous body diameter, extends between a percutaneous device proximal end and a percutaneous device distal end, and is formed of a material of a first durometer hardness; and the elongated anchor body is generally tubular and extends between an anchor body proximal end and an anchor body distal end, is formed of a material of a second durometer hardness exceeding the first durometer hardness of the percutaneous body diameter, and has an anchor body length that exceeds the percutaneous body diameter sufficiently to enable the elongated anchor body to bridge the percutaneous passageway when deployed and tensioned by the tensioning filament engaged by the external attachment means, whereby the anchor body length and second durometer hardness provide resistance to retraction or advancement of the percutaneous device body out of or into the percutaneous passageway when a force is exerted on the percutaneous device body to retract or advance the percutaneous device body.

20. The percutaneous assembly of claim 1, wherein:

the elongated percutaneous device body extends between a percutaneous device proximal end and a percutaneous device distal end and is formed of a material of a first durometer hardness; and the elongated anchor body is generally tubular and extends between an anchor body proximal end and an anchor body distal end and is formed of a material of a second durometer hardness exceeding the first durometer hardness of the percutaneous body diameter.

21. The percutaneous assembly of claim 1, wherein:

the percutaneous device body is configured as a gastrostomy catheter having a gastrostomy catheter proximal end adapted to be located outside the skin and a gastrostomy catheter distal end adapted to be inserted through a percutaneous passageway formed as a stoma tract to locate the gastrostomy catheter distal end in the stomach cavity, the gastrostomy catheter formed with a gastrostomy catheter lumen extending between a proximal lumen end opening at the gastrostomy catheter proximal end and a distal lumen end opening at the gastrostomy catheter distal end to enable infusion of fluids thereto and into the stomach cavity; and the anchor body is adapted to bear against the stomach wall within the stomach cavity and laterally bridge the stoma tract opening in the stomach wall upon tensioning of the tensioning filament.

22. The percutaneous assembly of claim 1, wherein:

the percutaneous device body is configured as a jejunostomy catheter having a jejunostomy catheter proximal end adapted to be located outside the skin and a jejunostomy catheter distal end adapted to be inserted through a percutaneous passageway formed as a stoma tract into the stomach cavity and through the stomach cavity to locate the jejunostomy catheter distal end in the small intestine, the jejunostomy catheter formed with a jejunostomy catheter lumen extending between a proximal lumen end opening at the jejunostomy catheter proximal end and a distal lumen end opening at the jejunostomy catheter distal end to enable infusion of fluids thereto and into the small intestine; and the anchor body is adapted to bear against the stomach wall within the stomach cavity and bridge the stoma tract opening in the stomach wall upon tensioning of the tensioning filament.

23. The percutaneous assembly of claim 1, wherein:

the percutaneous device body is configured as a gastro-jejunal catheter integrally formed of a gastrostomy catheter body and a jejunostomy catheter body adapted to be inserted through a percutaneous passageway formed as a stoma tract through the stomach cavity and into the small intestine, the gastrostomy catheter body having a gastrostomy catheter proximal end adapted to be located outside the skin and a gastrostomy catheter distal end adapted to be inserted through the stoma tract and into the stomach cavity, the gastrostomy catheter body formed with a gastrostomy catheter lumen extending between a proximal gastrostomy catheter lumen end opening at the gastrostomy catheter proximal end and a distal gastrostomy catheter lumen end opening at the gastrostomy catheter distal end to enable infusion of fluids thereto and into the stomach cavity;

the jejunostomy catheter body having a jejunostomy catheter proximal end adapted to be located outside the skin and a jejunostomy catheter distal end adapted to be inserted through the stoma tract into the stomach cavity and through the stomach cavity to locate the jejunostomy catheter distal end in the small intestine, the jejunostomy catheter formed with a jejunostomy catheter lumen extending between a proximal jejunostomy catheter lumen end opening at the jejunostomy catheter proximal end and a distal jejunostomy catheter lumen end opening at the jejunostomy catheter distal end to enable infusion of fluids thereto and into the small intestine; and the anchor body is adapted to bear against the stomach wall within the stomach cavity and bridge the stoma tract opening in the stomach wall upon tensioning of the tensioning filament.

24. The integrally formed gastro-jejunal catheter percutaneous assembly of claim 23, wherein:

the gastrostomy catheter body and the jejunostomy catheter body are integrally formed in a co-axial arrangement such that the jejunostomy catheter body extends through the gastrostomy catheter lumen, and the gastrostomy catheter distal end terminates proximally to the jejunostomy catheter distal end;

the elongated anchor body extends between an anchor body proximal end and an anchor body distal end; and the percutaneous assembly further comprises:

coupling means for coupling the anchor body proximal end with the jejunostomy catheter distal end for supporting the anchor body in axial alignment with the jejunostomy catheter body during insertion through the stoma tract; and release means for selectively releasing the anchor body proximal end from the coupling means after insertion of the jejunostomy catheter distal end through the stoma tract and in the stomach cavity to deploy the anchor body extending against the stomach wall and laterally across the stoma tract and the percutaneous device body.

25. The integrally formed gastro-jejunal catheter percutaneous assembly of claim 23, wherein:

the gastrostomy catheter body and the jejunostomy catheter body are integrally formed in a side-by-side arrangement such that the jejunostomy catheter body extends alongside the gastrostomy catheter body, and the gastrostomy catheter distal end terminates proximally to the jejunostomy catheter distal end;

the elongated anchor body extends between an anchor body proximal end and an anchor body distal end; and the percutaneous assembly further comprises:

coupling means for coupling the anchor body proximal end and with either the jejunostomy catheter distal end or the gastrostomy catheter distal end for supporting the anchor body in axial alignment with the gastro-jejunal catheter during insertion through the stoma tract; and release means for selectively releasing the anchor body proximal end from the coupling means after insertion of the catheter body distal end that the elongated anchor body extends from through the stoma tract and in the stomach cavity to deploy the anchor body extending against the stomach wall and laterally across the stoma tract and the percutaneous device body.

26. A method for fixing a percutaneous device having a percutaneous body extending between a percutaneous device proximal end and a percutaneous device distal end at its point of percutaneous insertion through a percutaneous passageway into a patient's body which comprises the steps of:

inserting an implantable anchor comprising an elongated anchor body and a tensioning filament coupled to the anchor body through the percutaneous passageway to be deployed subcutaneously in engagement with body tissue such that the tensioning filament extends through the percutaneous passageway and terminates outside the patient's body;

inserting the percutaneous device body through the percutaneous passageway to locate the percutaneous device distal end at a desired subcutaneous body site;

tensioning the tensioning filament to draw the anchor body against body tissue and extending across the percutaneous passageway; and attaching the tensioning filament to the percutaneous device body outside the patient's body, whereby the assembly of the deployed anchor within the patient's body with the percutaneous device body outside the patient's body inhibits advancement or retraction of the percutaneous device body through the percutaneous passageway.

27. The method of claim 26, wherein the anchor body is formed with an elongated anchor body channel extending axially between the anchor body ends, and the step of inserting the anchor body through the percutaneous passageway further comprises the steps of:

inserting a guidewire through the percutaneous passageway to the desired site;

fitting the elongated anchor body channel over the guidewire; and advancing the elongated anchor body over the guidewire to the desired site.

28. The method of claim 26, wherein the anchor body is formed with an anchor body width and an anchor body length exceeding the anchor body width and extending from and anchor body proximal end to an anchor body distal end, and the tensioning filament is attached to the elongated anchor body intermediate the anchor body proximal and distal ends, and wherein:

the step of inserting the anchor body through the percutaneous passageway comprises aligning the elongated anchor body length axially with and axially advancing the anchor body through the percutaneous passageway, and the step of tensioning the tensioning filament comprises retracting the tensioning filament to cause the anchor body to pivot into a transverse orientation with respect to the percutaneous passageway to bridge the percutaneous passageway and inhibit its retraction out of the percutaneous passageway.

29. The method of claim 26, wherein the percutaneous device body is formed with a percutaneous device lumen extending between a proximal lumen end opening at the percutaneous device proximal end and a distal lumen end opening at the percutaneous device distal end, and the steps of inserting the anchor body and the percutaneous device body through the percutaneous passageway further comprise the steps of:

fitting a coupling member of the elongated anchor body to the percutaneous device distal end in axial alignment with the percutaneous device body as a percutaneous assembly;

advancing the percutaneous assembly of the elongated percutaneous device body and anchor body through the percutaneous passageway to the desired site; and extending an elongated pusher through the percutaneous device lumen from the percutaneous device proximal end to the percutaneous device distal end and against the coupling member to release the anchor body from the percutaneous device distal end at the desired site.

30. The method of claim 26, wherein the percutaneous device body is formed with a percutaneous device lumen extending between a proximal lumen end opening at the percutaneous device proximal end and a distal lumen end opening at the percutaneous device distal end, and the steps of inserting the anchor body and the percutaneous device body through the percutaneous passageway further comprise the steps of:

advancing an elongated inner liner having an liner lumen and extending between an liner proximal end and an liner distal end into the proximal lumen end opening and through the percutaneous device lumen to position the liner distal end in an advanced position, fitting the elongated anchor body to the liner distal end in axial alignment with the percutaneous device body as a percutaneous assembly;

advancing the percutaneous assembly of the elongated percutaneous device body and anchor body through the percutaneous passageway to the desired site; and retracing the inner liner proximally to release the anchor body from the liner distal end at the desired site.

31. The method of claim 26, wherein the percutaneous device body is formed with a percutaneous device lumen extending between a proximal lumen end opening at the percutaneous device proximal end and a distal lumen end opening at the percutaneous device distal end, and the steps of inserting the anchor body and the percutaneous device body through the percutaneous passageway further comprise the steps of:

extending an elongated coupling element distally through the percutaneous device lumen;

releasably coupling the elongated anchor body to the elongated coupling element to extend the anchor body in axial alignment with the percutaneous device body as a percutaneous assembly;

advancing the percutaneous assembly of the elongated percutaneous device body and anchor body through the percutaneous passageway to the desired site; and manipulating the coupling element to release the anchor body from the liner distal end at the desired site.

32. The method of claim 26, wherein the anchor body is formed with an anchor body channel extending axially between the anchor body ends and a tensioning filament is attached to the elongated anchor body intermediate the anchor body ends, and the step of inserting the anchor body through the percutaneous passageway further comprises the steps of:

inserting a guidewire through the percutaneous passageway to the desired site;

fitting the elongated anchor body channel over the guidewire;

advancing the elongated anchor body over the guidewire to the desired body site; and releasing the guidewire from the anchor body channel leaving the anchor body at the desired site.

33. The method of claim 26, wherein the steps of insering the anchor body and the percutaneous device body through the percutaneous passageway further comprise the steps of:

fitting the elongated anchor body to the percutaneous device distal end in axial alignment with the percutaneous device body as a percutaneous assembly;

advancing the percutaneous assembly of the elongated percutaneous device body and anchor body through the percutaneous passageway to the desired site; and releasing the anchor body from the percutaneous device distal end at the desired site.

34. The method of claim 26, wherein the anchor body is formed with an elongated anchor body channel extending axially between the anchor body ends, the percutaneous device body is formed with a percutaneous device lumen extending between a proximal lumen end opening at the percutaneous device proximal end and a distal lumen end opening at the percutaneous device distal end, and the steps of inserting the anchor body and the percutaneous device body through the percutaneous passageway further comprise the steps of:

inserting a guidewire through the percutaneous passageway to the desired site;

fitting the elongated anchor body channel and the percutaneous device lumen over the guidewire;

advancing the elongated percutaneous device body and anchor body over the guidewire to the desired body site; and releasing the anchor body from the guidewire.

35. The method of claim 26, wherein the anchor body is formed with an elongated anchor body channel extending axially between the anchor body ends, the percutaneous device body is formed with a percutaneous device lumen extending between a proximal lumen end opening at the percutaneous device proximal end and a distal lumen end opening at the percutaneous device distal end, and the steps of inserting the anchor body and the percutaneous device body through the percutaneous passageway further comprise the steps of:

inserting a guidewire through the percutaneous passageway to the desired site;

fitting the elongated anchor body to the percutaneous device distal end in axial alignment with the percutaneous device body as a percutaneous assembly;

fitting the elongated anchor body channel and the percutaneous device lumen over the guidewire;

advancing the percutaneous assembly of the elongated percutaneous device body and anchor body over the guidewire through the percutaneous passageway to the desired site; and releasing the anchor body from the percutaneous device distal end and the anchor body from the guidewire at the desired site.

36. The method of claim 26, wherein the percutaneous device body is formed with a percutaneous device lumen extending between a proximal lumen end opening at the percutaneous device proximal end and a distal lumen end opening at the percutaneous device distal end, and the steps of inserting the anchor body and the percutaneous device body through the percutaneous passageway further comprise the steps of:

advancing an elongated inner liner having an liner lumen and extending between an liner proximal end and an liner distal end into the proximal lumen end opening and through the percutaneous device lumen to position the liner distal end in an advanced position;

fitting the elongated anchor body to the liner distal end in axial alignment with the percutaneous device body as a percutaneous assembly;

inserting a guidewire through the percutaneous passageway to the desired site;

fitting the elongated anchor body and the liner lumen over the guidewire;

advancing the percutaneous assembly of the elongated percutaneous device body and anchor body over the guidewire through the percutaneous passageway to the desired site; and retracting the inner liner proximally to release the anchor body from the liner distal end and the guidewire at the desired site.

37. The method of claim 36, wherein the anchor body is formed with an anchor body width and an anchor body length exceeding the anchor body width and extending from and anchor body proximal end to an anchor body distal end and with an elongated anchor body channel open to the anchor body side wall extending axially between the anchor body ends, and wherein:

the step of fitting the anchor body and the liner lumen over the guidewire further comprises the steps of:

inserting the anchor body proximal end into the liner lumen the distal end of the inner liner, whereby the inner liner closes a proximal segment of the anchor body channel; and fitting the guidewire through the percutaneous device lumen and through the elongated anchor body channel; and the retracting step further comprises the step of retracting the inner liner from the anchor body proximal end to fully open the anchor body channel and allow the anchor body to distally separate from the percutaneous device body and laterally separate from the guidewire.

\* \* \* \* \*